US008603751B2

(12) United States Patent
Steyn et al.

(10) Patent No.: US 8,603,751 B2
(45) Date of Patent: Dec. 10, 2013

(54) MYCOBACTERIAL DISEASE DETECTION, TREATMENT, AND DRUG DISCOVERY

(75) Inventors: Andries J. C. Steyn, Hoover, AL (US); Deborah Mai, Tuscaloosa, AL (US); Amit Singh, Hoover, AL (US)

(73) Assignee: The UAB Research Foundation, Birmingham, AL (US)

( * ) Notice: Subject to any disclaimer, the term of this patent is extended or adjusted under 35 U.S.C. 154(b) by 261 days.

(21) Appl. No.: 12/281,082

(22) PCT Filed: Mar. 1, 2007

(86) PCT No.: PCT/US2007/063099
§ 371 (c)(1),
(2), (4) Date: Sep. 29, 2008

(87) PCT Pub. No.: WO2007/101274
PCT Pub. Date: Sep. 7, 2007

(65) Prior Publication Data
US 2009/0068197 A1 Mar. 12, 2009

Related U.S. Application Data

(60) Provisional application No. 60/872,366, filed on Dec. 1, 2006, provisional application No. 60/778,307, filed on Mar. 2, 2006.

(51) Int. Cl.
*G01N 33/53* (2006.01)
(52) U.S. Cl.
USPC .......................................................... 435/7.1
(58) Field of Classification Search
None
See application file for complete search history.

(56) References Cited

U.S. PATENT DOCUMENTS

| | | | |
|---|---|---|---|
| 4,960,872 A | 10/1990 | Schlafer et al. | |
| 5,444,094 A | 8/1995 | Malik et al. | |
| 5,985,935 A | 11/1999 | Kharazimi et al. | |
| 6,228,371 B1 * | 5/2001 | Nano | 424/248.1 |
| 6,235,680 B1 * | 5/2001 | Ziemer et al. | 504/112 |
| 2002/0106698 A1 | 8/2002 | Manfredi | |
| 2003/0236393 A1 * | 12/2003 | Trucksis | 536/23.1 |
| 2004/0241826 A1 * | 12/2004 | James et al. | 435/252.3 |

FOREIGN PATENT DOCUMENTS

| | | |
|---|---|---|
| WO | WO/02/054073 | 7/2002 |
| WO | WO03106430 | 12/2003 |
| WO | WO/2004/067718 | 8/2004 |
| WO | WO 2005/007822 | 1/2005 |
| WO | WO2005014585 | 2/2005 |
| WO | WO2006079057 | 7/2006 |

OTHER PUBLICATIONS

Cruse et al., Illustrated Dict. of Immunology, 2nd ed., CRC Press, 2003, p. 46, 166, 382.*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992.*
Murray et al. (Medical Microbiol., 4th ed., Mosby Press, 2002, pp. 170-172.*
Murray et al. (Medical Microbiol., 4th ed., 2002, pp. 170-172).*
Chackalamannil s. et al., "Potent, low molecular weight thrombin receptor antagonists"; Bioorganic & Medicinal Chemistry Letters, Pergamon, Elsevier Science, GB, vol. 11, No. 21, Nov. 1, 2001, pp. 2851-2853.
Mayfield & Deruiter, Novel inhibitors of rat lens aldose reductase: N-[[(Substituted amino) phenyl]sulfonyl]glycines: J. Med. chem.., vol. 30, 1987, pp. 1595-1598.
Daniels & Iwamoto, "N1, N4-Nicotinyl derivatives of sulfanilamide" Journal of the American Chemical Society, vol. 62, 1940, pp. 741-742.
European Search Report in related EP Application No. EP 07 75 7743 dated Mar. 1, 2010.
Singh et al. "Dissecting Virulence Pathways of *Mycobacterium Tuberculosis* Through Protein-Protein Association" *PNAS*, vol. 103, No. 30 (Jul. 25, 2006) pp. 11346-11351.
Okkels, L M. et al., "Protein-Protein Interactions of Proteins from the ESAT-6 Family of *Mycobacterium tuberculosis*," J. Bacteriology, v. 186, pp. 2487-2491, (2004).
Stanley, S.A., "Acute Infection and Macrophage Subversion of *Mycobacterium tuberculosis* require a Specialized Secretion System," Proc. Natl. Acad. Sci., v. 100, pp. 13001-13006.
Partial European Search Report dated Feb. 22, 2013 for EP Application No. 12170928.1.
XP002691425 retrieved from EBI accession No. Uniprot P95032 (May 1, 1997); Partial European Search Report dated Feb. 22, 2013 for EP Application No. 12170928.1.
XP002691426 retrieved from EBI accession No. Uniprot O53579 (Jun. 1, 1998); Partial European Search Report dated Feb. 22, 2013 for EP Application No. 12170928.1.
XP002691427 retrieved from EBI accession No. Uniprot P0A522 (Mar. 15, 2005); Partial European Search Report dated Feb. 22, 2013 for EP Application No. 12170928.1.
XP002691428 retrieved from EBI accession No. Uniprot Q10522 (Oct. 1, 1996); Partial European Search Report dated Feb. 22, 2013 for EP Application No. 12170928.
XP002691429 retrieved from EBI accession No. Uniprot P64168 (Oct. 11, 2004) Partial European Search Report dated Feb. 22, 2013 for EP Application No. 12170928.
European Patent Application No. 12170928.1, Extended European Search Report, mailed Jun. 20, 2013, 17 pages.
Japanese Patent Application No. 2008557501, Office Action, mailed Oct. 29, 2012, 4 pages.

* cited by examiner

*Primary Examiner* — Brian J Gangle
(74) *Attorney, Agent, or Firm* — Kilpatrick, Townsend & Stockton LLP

(57) ABSTRACT

Methods for detecting and treating *Mycobacterium*-related diseases including reducing Mycobacterial virulence, reducing RV3133c dimerization, and treating a subject with a Mycobacterial infection using identified compounds are disclosed. Examples of compounds useful in the treatment of *Mycobacterium*-related diseases include N-(4-[(acetylamino)sulfonyl]phenyl)-3-phenylpropanamide; 1-(3,5-di-tert-butyl-4-hydroxyphenyl)-2-(2-imino-3-methyl-2,3-dihydro-1H-benzimidazol-1yl)ethanone hydrochloride; and 1-(1, 3-benzoxazol-2-yl)-3-({4-[(2-hydroxyethyl)sulfonyl]phenyl}amino)acrylaldehyde. Further disclosed are methods for identifying agents that interact with a polypeptide in a *Mycobacterium* cell.

3 Claims, 12 Drawing Sheets

MYCOBACTERIAL DISEASE DETECTION, TREATMENT, AND DRUG DISCOVERY

CROSS-REFERENCE TO RELATED APPLICATIONS

This application claims priority to U.S. Application Ser. No. 60/778,307, which was filed on Mar. 2, 2006; and U.S. Application Ser. No. 60/872,366, which was filed on Dec. 1, 2006, each of which is incorporated by reference herein in its entirety.

BACKGROUND

Mtb (*Mycobacterium tuberculosis*) is responsible for 2-3 million deaths annually (WHO, 2004). Despite major technical advancements in extracting information from genome sequences, gene function can only be attributed to ~58% of the ORFs of Mtb emphasizing the importance of developing novel and creative approaches to better understand gene function and thus, virulence. A key challenge in the post-genomic era is to integrate functional strategies to better understand the molecular mechanism of Mtb virulence. It has become increasingly clear that virulence pathways are mediated by multipart networks of molecular connections and that Mtb fails to execute its function unless it interacts with other proteins. It has also been recognized that physical association between a protein of unknown function and a known protein indicates that the former often has a function related to that of the latter. Furthermore, the development of an in vivo technology to study protein-protein association in genetically intractable pathogens, such as Mtb, can significantly impact the understanding of the mechanism of disease.

SUMMARY

Methods, materials, and kits for detecting and treating *Mycobacterium*-related infections in a subject, such as tuberculosis, as well as methods for identifying Mycobacterial proteins, drugs, and drug targets are disclosed herein.

Methods for detecting Mycobacterial infection and identifying agents that indicate Mycobacterial infection that utilize identified proteins and protein-protein interactions are disclosed. For example, specific proteins useful for the detection of Mycobacterial infection include Rv0686, Rv2151c, Rv2240c, Rv3596c, Rv3800c, Cfp-10 (Rv3874), and Esat-6 (Rv3875).

Methods for reducing Mycobacterial virulence, reducing RV3133c dimerization, and treating a subject with a Mycobacterial infection using compounds with the following general formula are disclosed:

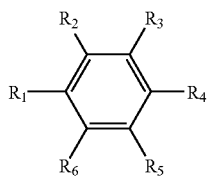

wherein:

$R_1$ is NH—X or C(=O)—X, wherein X is a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl;

$R_4$ is OH; $SO_2$—Y, wherein Y is a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl; or $SO_2$—NH—Z, wherein Z is a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl; and each of $R_2$, $R_3$, $R_5$, and $R_6$ is independently H, OH, a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl.

Examples of such compounds include N-(4-[(acetylamino)sulfonyl]phenyl)-3-phenylpropanamide; 1-(3,5-di-tert-butyl-4-hydroxyphenyl)-2-(2-imino-3-methyl-2,3-dihydro-1H-benzimidazol-1yl)ethanone hydrochloride; and 1-(1,3-benzoxazol-2-yl)-3-({4-[(2-hydroxyethyl)sulfonyl]phenyl}amino)acrylaldehyde.

Further disclosed is a method for identifying an agent that interacts with a polypeptide in a *Mycobacterium* cell. In this method, a first fusion protein comprising a first fragment of an enzyme reporter molecule and a first polypeptide and a second fusion protein comprising a second fragment of the enzyme reporter molecule are combined. After combination, association of the first and second polypeptides results in reassembly of the enzyme reporter molecule and reconstitution of the enzyme reporter activity. Finally, enzyme reporter activity is detected. A change in the activity of the reporter molecule indicates that the agent is interacting with the second polypeptide. With this system, agents that either facilitate or inhibit interactions between the first and second polypeptides can be identified.

DETAILED DESCRIPTION OF THE INVENTION

Figure 1:
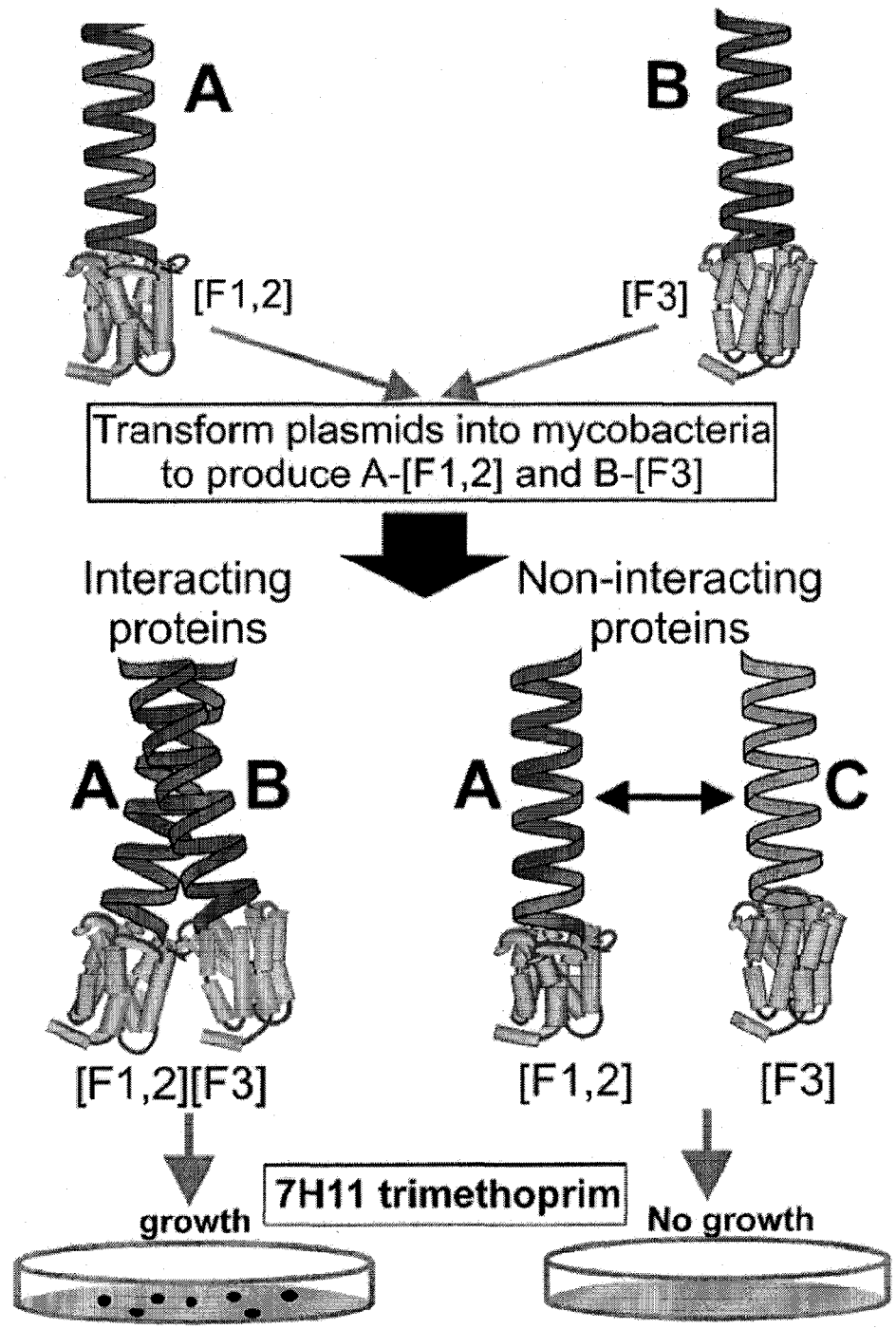
FIG. 1 is an illustration depicting the mycobacterial-protein fragmentation complementation (M-PFC) technique.

Detection and treatment of tuberculosis infections are important measures in the fight against this epidemic, especially in industrialized countries. The tuberculin skin test (TST) has been the only practical means of detecting latent *M. tuberculosis* infection in the past century. Unfortunately, the TST suffers from a number of well-documented performance and logistic problems, the most serious being false-positive responses due to reactivity caused either by infection with nontuberculous mycobacteria (NTM), or by *bacillus* Calmette-Guérin (BCG) vaccination. An in vitro whole blood test that detects *M. tuberculosis* infection by measuring IFN-responses to tuberculin purified protein derivative (PPD) was approved in the United States. Although this assay may be less affected by the BCG vaccination than the TST, it is falsely positive in some BCG-vaccinated individuals as many PPD antigens are similar or identical to antigens in BCG and NTM. Parts of the *M. tuberculosis* genome that are absent from the genomes of all BCG substrains and most NTM have been identified. These *M. tuberculosis*-specific regions encode a number of proteins including Cfp-10 and Esat-6. Cell-mediated responses to these antigens have been shown to correlate with both proven *M. tuberculosis* infection and a high risk of infection. However, the application of Cfp-10 and Esat-6 to the whole blood IFN-assay, while it allows for a more sensitive diagnosis of *M. tuberculosis* infection, still has limitations, as it cannot discriminate in the severity of the infection, and still results in false negatives and positives. Furthermore, estimates of sensitivity and specificity of tests for *M. tuberculosis* infection are hampered by the lack of a gold standard; one cannot prove the presence or absence of latent tuberculosis (TB) infection.

Methods and compositions for the detection and treatment of mycobacterial infection are disclosed herein. Further, methods for identifying agents useful in the detection and treatment of mycobacterial infection are also disclosed herein. In order to study mycobacterial disease and pathogenesis, a mycobacterial system has been developed that allows for the study of protein-protein associations in mycobacteria. This system, called the mycobacterial protein fragment complementation (M-PFC) system, is based upon the functional reconstitution in the model organism *Mycobacterium smegmatis* (Msm) of two small murine dihydrofolate reductase (mDHFR) domains independently fused to two interacting proteins. Using M-PFC, dimerization of yeast GCN4, interaction between the Mtb histidine kinase KdpD and response regulator KdpE, and association between the secreted antigens Esat-6 and Cfp-10 has been successfully demonstrated. The association between the membrane-spanning sensor kinase, DevS and response regulator DevR, has also been successfully shown, thereby demonstrating the ability of M-PFC to reveal protein associations in the mycobacterial membrane. An Mtb H37Rv library was screened for proteins that associate with the major secreted antigen Cfp-10, and Esat-6 (a protein known to associate with Cfp-10) was consistently found in the screens.

Cfp-10 was also found to associate with the following proteins: (1) Rv0686 and Rv2151c (FtsQ), a component and substrate respectively, of the evolutionary conserved signal recognition pathway (SRP); (2) Rv3596c (ClpC1), an AAA-ATPase chaperone involved in protein translocation and quality control; (3) Rv2240c, which previously had no known function; and (4) Rv3800c (pks13), a polyketide synthase that catalyzes the last step of mycolic acid biosynthesis. These results directly link the Mtb signal peptide independent secretion (SPS) pathway with the evolutionary conserved SRP and SecA/SecYEG pathways, showing that they can share secretory components.

Because of the association of Rv0686, Rv2151c, Rv2240c, Rv3596c, and Rv3800c with Cfp-10 and Esat-10, these proteins can be used in various methods, kits, and assays related to the detection of tuberculosis. These proteins can also be used to detect leprosy and other Mycobacterial diseases. Such applications of these proteins to the detection and treatment of tuberculosis, leprosy, and other *Mycobacterium*-related diseases and disorders are discussed below.

Methods of detecting tuberculosis infection in a subject involve detecting one or a combination of the following polypeptides: Rv0686, Rv2151c, Rv2240c, Rv3596c, Rv3800c or a fragment thereof in a sample from the subject. Detection of one or more of these polypeptides indicates an tuberculosis infection. Detection of Cfp-10 (Rv3874) and/or Esat-6 (Rv3875) also indicates a tuberculous infection. Such detection can take place using a whole blood IFN-γ assay, for example, or using a nucleic acid detection system (e.g., a nucleic acid encoding the polypeptide is detected using a PCR detection system).

As used herein, a subject is an individual. Thus, the subject can be, but is not limited to, domesticated animals (such as cats, dogs, etc.), livestock (e.g., cattle, horses, pigs, sheep, goats, etc.), laboratory animals (e.g., mouse, rabbit, rat, guinea pig, etc.) and birds. For further example, the subject can be a mammal such as a primate, or a human.

The methods and assays described herein are useful in diagnosing as well as treating individuals with both latent (LTBI) and active tuberculosis (TB) infections. Except for very young children, few people display tuberculosis symptoms immediately after primary infection. However, in latent infections, the bacteria are harbored in macrophages. In macrophages, the bacteria can remain alive in a dormant state for many years, walled off inside tiny scars. In 90 to 95% of cases, the bacteria never cause any further problem, but in about 5 to 10% of infected people they start to multiply (active disease). It is in this active phase that an infected person actually becomes sick and can spread the disease.

Active infection is more often brought on in children, those with very advanced age, or by the use of corticosteroids. Like many infectious diseases, tuberculosis spreads more quickly and is much more dangerous in people who have a weakened immune system. Therefore, those with HIV infection are at an increased risk of developing active tuberculosis. It is known that treatment of latent tuberculosis infection (LTBI), also referred to as preventive therapy or chemoprophylaxis, helps to prevent progression to active disease in human immunodeficiency virus (HIV) negative populations.

An in vitro test can be used to diagnose *Mycobacterium tuberculosis* infection, including both latent tuberculosis infection (LTBI) and tuberculosis (TB) disease. For example, an enzyme-linked immunosorbent assay (ELISA) test detects the release of interferon-gamma (IFN-γ) in fresh heparinized whole blood from sensitized persons when it is incubated with mixtures of synthetic peptides simulating the proteins present in *M. tuberculosis*, such as Rv0686, Rv2151c, Rv2240c, Rv3596c, and Rv3800c, as described above, as well as early secretory antigenic target-6 (ESAT-6) and culture filtrate protein-10 (CFP-10).

For all of the methods and assays described herein, any of the following proteins (Rv0686, Rv2151c, Rv2240c, Rv3596c, and Rv3800c) can be detected individually, or in any combination. While one of the listed proteins is sufficient to detect the presence of a tuberculosis infection, they can be used in various combinations as well. As used herein, the term in combination is meant simultaneously or sequentially. The following list is not limiting, but serves as an example of some of the combinations that are possible. For instance, each of the proteins Rv0686, Rv2151c, Rv2240c, Rv3596c, or Rv3800c can be detected alone using the methods and assays disclosed herein. Rv0686 can also be detected with Rv2151c. Rv0686 can also be detected with Rv2240c. Rv0686 can also be detected with Rv3596c. Rv0686 can also be detected with Rv3800c. Furthermore, Rv0686, Rv2151c, and Rv2240c can be detected together. Rv0686, Rv2151c, Rv2240c, and Rv3596c can also be detected together. Rv0686, Rv2240c, Rv3596c, and Rv3800c can also be detected together. Rv0686, Rv3596c, and Rv3800c can also be detected together. Rv0686, Rv2151c, Rv3596c, and Rv3800c can also be detected together. Rv0686, Rv3596c, and Rv3800c can also be detected together. Rv2151c, Rv2240c, Rv3596c, and Rv3800c can also be detected together. Rv2240c, Rv3596c, and Rv3800c can also be detected together. Rv3596c and Rv3800c can also be detected together. Rv2151c, Rv3596c, and Rv3800c can also be detected together. The above list is not complete, and is not limiting, but serves as an example of some of the combinations that are possible.

Further to the above combinations of proteins, Cfp-10 and Esat-10 can also be used in the methods and assays used to detect tuberculosis infection. Cfp-10 and Esat-10 can be used in combination with each other and the other various protein combinations possible, or can be used individually and the other various protein combinations possible For example, Rv0686 and Cfp-10 can be detected, or Rv0686, Cfp-10, and Esat-6 can be detected. This is only one example of the many combinations possible.

Also disclosed herein is a method of detecting the presence of tuberculosis in a subject, comprising the steps of: a) contacting a biological sample obtained from a subject, wherein said biological sample comprises antibodies against one of more of Rv0686, Rv2151c, Rv2240c, Rv3596c, or Rv3800c, or a fragment thereof; and b) detecting in the sample an amount of antibody that binds to one or more of the polypeptide(s), wherein binding of one or more of Rv0686, Rv2151c, Rv2240c, Rv3596c, Rv3800c, or a fragment thereof to an antibody in the sample indicates the presence of tuberculosis in the subject. Rv3596c, for example, has been shown to be detectable by an antibody assay. Cfp-10 and/or Esat-6 can also be detected, for example.

The interaction of these Rv proteins (Rv0686, Rv2151c, Rv2240c, Rv3596c, and Rv3800c) with Esat-6 and/or Cfp-10 can affect IFN-γ levels. The lymphokine IFN-γ, produced primarily by T cells and NK cells, has been shown to be an important mediator of macrophage activation in controlling a number of intracellular pathogens. IFN-γ mRNA has been found in pleural tissues from tuberculosis patients and in the lesions of the self-healing form of leprosy. Injection of recombinant IFN-γ into lesions in lepromatous leprosy patients resulted in the migration of large numbers of Th cells and monocytes to the site of injection and a decrease in acid-fast bacilli. T cells which adoptively transferred protection against a virulent *M. tuberculosis* challenge produce IFN-γ when stimulated in vitro.

Also disclosed herein is a method of monitoring the progression of tuberculosis in a subject, comprising the steps of contacting a biological sample obtained from a subject, wherein said biological sample comprises antibodies, with one or more Rv0686, Rv2151c, Rv2240c, Rv3596c, Rv3800c, Cfp-10 Esa-o, or a fragment thereof; detecting in the sample an amount of antibody that binds to the polypeptide(s); and repeating the previous steps using a biological sample obtained from the subject at one or more subsequent points in time; an increase in the amount of bound antibody indicating a progression of tuberculosis in the subject. IFN-γ production can be measured using the method described above.

Disclosed herein is a method of detecting severity of a tuberculosis infection in a subject comprising detecting the amount of one or more of Rv0686, Rv2151c, Rv2240c, Rv3596c, Rv3800c, or a fragment thereof; and comparing the amount of the polypeptide to a standard, wherein the severity of the tuberculosis infection can be determined by the amount of the polypeptide.

Also disclosed is a method of decreasing a bacterial infection in a cell comprising modulating activity of one or more of the following polypeptides: Rv0686, Rv2151c, Rv2240c, Rv3596c, and Rv3800c. The bacterial infection can be caused by *Mycobacterium*. Specifically, *Mycobacterium tuberculosis, M. leprae, M. ulcerans, M. avium*, or *M. marinum*, for example. Activity of the polypeptides can be modulated by contacting the cell with a composition comprising a chemical, a compound, a small or large molecule, an organic molecule, an inorganic molecule, a peptide, a drug, a protein, an antibody, a morpholino, a triple helix molecule, an siRNA, an shRNAs, an miRNA, an antisense nucleic acid, or a ribozyme. In one example, the bacterial infection is modulated by an antibody that specifically binds to the polypeptide. Such embodiments are discussed in more detail below. Furthermore, the cell can be in a subject or in vitro.

Disclosed is a method of identifying an agent that modulates interaction between Cfp-10 and Rv0686, Rv2151c, Rv2240c, Rv3596c, or Rv3800c comprising: administering the agent in the presence of Cfp-10 and Rv0686, Rv2151c, Rv2240c, Rv3596c, or Rv3800c; detecting interaction between Cfp-10 and Rv0686, Rv2151c, Rv2240c, Rv3596c, or Rv3800c, a change in interaction indicating a compound that modulates interaction.

Also disclosed is a method of identifying an agent that modulates interaction between Cfp-10 and Rv0686, Rv2151c, Rv2240c, Rv3596c, or Rv3800c comprising: contacting a cell expressing Cfp-10 and Rv0686, Rv2151c, Rv2240c, Rv3596c, or Rv3800c with the agent; detecting interaction between Cfp-10 and Rv0686, Rv2151c, Rv2240c, Rv3596c, or Rv3800c, a change in interaction (e.g., a change in the level of binding) indicating a compound that modulates interaction.

Also disclosed is a method of identifying an agent that modulates interaction between Esat-6 and Rv0686, Rv2151c, Rv2240c, Rv3596c, or Rv3800c comprising: administering the agent in the presence of Esat-6 and Rv0686, Rv2151c, Rv2240c, Rv3596c or Rv3800c; and detecting interaction between Esat-6 and Rv0686, Rv2151c, Rv2240c, Rv3596c, or Rv3800c, a change in interaction indicating a compound that modulates interaction.

Also disclosed is a method of identifying an agent that modulates interaction between Esat-6 and Rv0686, Rv2151c, Rv2240c, Rv3596c, or Rv3800c comprising: contacting a cell expressing Esat-6 and Rv0686, Rv2151c, Rv2240c, Rv3596c or Rv3800c with the agent; and detecting interaction between Esat-6 and Rv0686, Rv2151c, Rv2240c, Rv3596c, or Rv3800c, a change in interaction indicating a compound that modulates interaction.

Disclosed herein is a method of identifying an agent that decreases bacterial infection in a cell comprising contacting a cell that expresses Rv0686, Rv2151c, Rv2240c, Rv3596c, or Rv3800c with the agent; and detecting a change in the expression or activity of Rv0686, Rv2151c, Rv2240c, Rv3596c, or Rv3800c, a change in expression or activity indicating that the agent is an agent that decreases bacterial infection. The cell can be in a subject or in vitro.

Disclosed herein is an immunogenic composition comprising one or more of Rv0686, Rv2151c, Rv2240c, Rv3596c, Rv3800c, or an immunogenic fragment thereof. The composition can further comprise a carrier and/or an adjuvant.

Also disclosed is a diagnostic assay for detecting tuberculosis infection comprising a means of detecting one of more of Rv0686, Rv2151c, Rv2240c, Rv3596c, or Rv3800c or a means of detecting how Rv0686, Rv2151c, Rv2240c, Rv3596c, or Rv3800c modifies Esat-6 and/or Cfp-10 to affect IFN-γ (which can be measured via ELISA). In this assay, Cfp-10 and/or Esat-6 can also be detected. In one example, the means of detection can be ELISA.

Also disclosed herein is a diagnostic assay for determining severity of a tuberculosis infection comprising a means of detecting the amount of one or more of Rv0686, Rv2151c, Rv2240c, Rv3596c, or Rv3800c or a means of detecting how Rv0686, Rv2151c, Rv2240c, Rv3596c, or Rv3800c modifies Esat-6 and/or Cfp-10. In this assay, Cfp-10 and/or Esat-6 can also be detected. In one example, the means of detection can be ELISA.

Also disclosed herein is an isolated antibody, or antigen-binding fragment thereof, that specifically binds to Rv0686, Rv2151c, Rv2240c, Rv3596c, Rv3800c or an immunogenic fragment thereof. For example, the antibody can be a neutralizing antibody.

Also disclosed herein is a microarray comprising probes for nucleic acids encoding one or more of the following polypeptides: Rv0686, Rv2151c, Rv2240c, Rv3596c, or Rv3800c. Microarrays, which can be used to detect antibodies to Rv0686, Rv2151c, Rv2240c, Rv3596c, or Rv3800c, are also provided comprising one or more of the listed polypeptides or fragments thereof. Also, provided herein are microarrays comprising antibodies to the listed polypeptides or antibody fragments that bind one or more of the listed polypeptides.

All of the above methods, assays, and kits can also used with leprosy (*M. leprae*) and other mycobacterial diseases. Specifically, disclosed herein is a method of detecting leprosy in a subject comprising detecting a response generated by immune cells using one or a combination of Rv0686, Rv2151c, Rv2240c, Rv3596c, Rv3800c, or a fragment thereof; in a sample from the subject, wherein a response generated by an immune cell indicates leprosy.

Also disclosed herein is a method of differentiating between immune responses generated by an *M. tuberculosis* infection and a memory response generated by vaccination in a subject comprising detecting a response generated by immune cells using one or a combination of the following polypeptides: Rv0686, Rv2151c, Rv2240c, Rv3596c, Rv3800c, or a fragment thereof, in a sample from the subject, wherein detection of one or more of the polypeptides indicates a tuberculosis infection instead of a vaccination. For example, the vaccination can be an *M. bovis* BCG vaccination.

Also disclosed are the components to be used to prepare the disclosed compositions as well as the compositions themselves to be used within the methods disclosed herein. These and other materials and methods are disclosed herein, and it is understood that when combinations, subsets, interactions, groups, etc. of these materials or steps of a method are disclosed that, while specific reference of each various individual and collective combinations and permutation of these compounds or steps may not be explicitly disclosed, each is specifically contemplated and described herein. For example, if a list of polypeptides is disclosed and discussed and the polypeptides can be used alone or in combination, specifically contemplated is each and every combination and permutation of polypeptides that are possible unless specifically indicated to the contrary. Thus, if a class of molecules or steps A, B, and C are disclosed as well as a class of molecules or steps D, E, and F and an example of a combination, A-D is disclosed, even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Those proteins disclosed herein, such as Rv0686, Rv2151c, Rv2240c, Rv3596c, Rv3800c, Cfp-10, and Esat-6 can have variants, derivatives, and can be used as fragments thereof that are also useful with the methods and assays described herein. One way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

As used herein, the term hybridization means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. Stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The terms higher, increases, elevates, or elevation refer to increases above basal or control levels. The term control as used herein is a standard by which a change is measured. For example, a control is not subjected to a test variable, but is instead subjected to a defined set of parameters, or the control is based on pre- or post-treatment levels. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987: 154:367, 1987 which is herein incorporated by reference in its entirety and at least for material related to hybridization of nucleic acids). As used herein, the term stringent hybridization with respect to a DNA:DNA hybridization is about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. The terms reduce, reduced, reduces, reduction, low, or lower refer to decreases below basal or control levels. Stringency of hybridization and washing, if desired, can be increased accordingly as homology desired is increased, and further, depending upon the G-C or A-T richness of any area wherein high homology is desired, all as known in the art.

The terms higher, increases, elevates, or elevation, as used herein, refer to increases above basal or control levels. The term control as used herein is a standard by which a change is measured. For example, a control is not subjected to a test variable, but is instead subjected to a defined set of parameters, or the control is based on pre- or post-treatment levels.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent of the primer molecules are extended. Preferred conditions also include those suggested by the manufacturer or indicated in the art as being appropriate for the enzyme performing the manipulation.

It is understood that those of skill in the art understand that if a composition or method meets any one of these criteria for determining hybridization either collectively or singly it is a composition or method that is disclosed herein.

The invention provides polypeptides related to mycobacterial antigens. As used herein, the term polypeptide is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Thus, a bacterial polypeptide or bacterial protein, or more specifically a mycobacterial polypeptide or mycobacterial protein, refers generally to a polypeptide sequence of the present invention that is present in samples isolated from a substantial proportion of subjects with those diseases disclosed herein. A polypeptide sequence of the invention, based upon its expression in infected cells, isolated from individuals with those diseases disclosed herein, has particular utility both as a diagnostic marker as well as a therapeutic agent, as further described below. The terms agent and target refer to a compound or other molecule to be tested for its ability to interact with a selected protein or other molecule. Examples of variations on the use of the term target, include, but are not limited to, target molecule, target substrate, target nucleic acid molecule, target region, target cell, and in each case refer to type of target. In one particular embodiment of the present invention, a bacterial polypeptide or bacterial protein comprises Rv3874 (Cfp-10), Rv3873 (Esat-6), Rv0686, Rv2151c, Rv2240c, Rv3596c, or Rv3800c.

Polypeptides described herein can be identified by their different reactivity with samples from subjects with tuberculosis, or other mycobacterial diseases, as compared to samples from unaffected individuals. For example, polypeptides described herein may be identified by their reactivity with samples from subjects with tuberculosis or other mycobacterial disease as compared to their lack of reactivity to samples from unaffected individuals. As used herein, the term lack of reactivity is meant any reactivity that is less that 1.5 times above background for a given assay method. As used herein, the terms reactivity or higher reactivity refer to a reactivity that is at least 1.5 times above the background for a given assay. Additionally, polypeptides described herein can be identified by their reactivity with samples from subjects with tuberculosis or other mycobacterial disease as compared to their higher reactivity to samples from unaffected individuals. Additionally, polypeptides described herein may be identified by their reactivity with samples from subjects with tuberculosis as compared to their lower reactivity to samples from unaffected individuals. As used herein, the term lower reactivity can be less than a comparison point and can include a lack of reactivity.

Optionally, the polypeptides or fragments thereof of the invention are immunogenic. Screening for immunogenic activity can be performed using techniques well known to the skilled artisan. For example, such screens can be performed using methods such as those described in Harlow and Lane, Antibodies: A Laboratory Manual, Cold Spring Harbor Laboratory, 1988. In one illustrative example, a polypeptide may be immobilized on a solid support and contacted with subject sera to allow binding of antibodies within the sera to the immobilized polypeptide(s).

Solid supports are solid-state substrates or supports with which molecules, such as analytes and analyte binding molecules, can be associated. Analytes, such as calcifying nanoparticles and proteins, can be associated with solid supports directly or indirectly. For example, analytes can be directly immobilized on solid supports. Analyte capture agents, such as capture compounds, can also be immobilized on solid supports. A preferred form of solid support is an array or chip. Another form of solid support is an array detector. An array detector is a solid support to which multiple different capture compounds or detection compounds have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A preferred form for a solid-state substrate is a microtiter dish, such as a standard 96-well type. In preferred embodiments, a multiwell glass slide can be employed that normally contain one array per well. This feature allows for greater control of assay reproducibility, increased throughput and sample handling, and ease of automation.

Different compounds can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array generally can have one type of component (that is, all the components at that location are the same). Each location will have multiple copies of the component. The spatial separation of different components in the array allows separate detection and identification of the polynucleotides or polypeptides disclosed herein.

Methods for immobilizing antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy] succinimide ester (GMBS). These and other attachment agents, as well as methods for their use in attachment, are described in *Protein immobilization. fundamentals and applications*, Richard F. Taylor, ed. (M. Dekker, New York, 1991); Johnstone and Thorpe, *Immunochemistry In Practice* (Blackwell Scientific Publications, Oxford, England, 1987) pages 209-216 and 241-242, and *Immobilized Affinity Ligands*; Craig T. Hermanson et al., eds. (Academic Press, New York, 1992) which are incorporated by reference in their entirety for methods of attaching antibodies to a solid-state substrate.

Each of the components immobilized on the solid support preferably is located in a different predefined region of the solid support. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components preferably are immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

Optionally, at least one address on the solid support is selected from the sequences or part of the sequences set forth in any of the proteins or nucleic acid sequences encoding the proteins disclosed herein. Solid supports can also comprise at least one address that is a variant of the sequences or part of the sequences set forth in any of the proteins or nucleic acid sequences encoding the proteins disclosed herein.

Also disclosed are antigen microarrays for multiplex characterization of antibody responses. For example, disclosed are antigen arrays and miniaturized antigen arrays to perform large-scale multiplexed characterization of antibody responses directed against the polypeptides, polynucleotides and antibodies described herein, using submicroliter quantities of biological samples as described in Robinson et al., Autoantigen microarrays for multiplex characterization of autoantibody responses, Nat Med., 8(3):295-301 (2002), which in herein incorporated by reference in its entirety for its teaching of constructing and using antigen arrays to perform large-scale multiplex characterization of antibody responses directed against structurally diverse antigens, using submicroliter quantities of biological samples.

The protein sequences for and respective nucleic acids encoding Rv0686, Rv2151c, Rv2240c, Rv3596c, Rv3800c, Cfp-10 (Rv 3874), and Esat 6 (Ru 3875) are disclosed herein. Information concerning *M. tuberculosis* genes and their associated proteins can be found at a website, operated by the University of California Los Angeles (UCLA) Institute for Proteomics and Genomics, which contains the entire *M. tuberculosis* genome, and contains information about *M. tuberculosis* genes and, when known, the function of their associated proteins. Such information includes, but is not limited to genomic information (for example, nucleic acid sequences), proteomic information (for example, protein sequences), functional information, homologous sequences, motifs and domains. The description of conservative substitutions and homology herein can be combined together in any combination, such as embodiments that have at least 70% homology to a particular sequence and wherein the variants comprise one or more conservative substitutions.

Furthermore, it is understood that there are numerous amino acid and peptide analogs which can be incorporated into the disclosed compositions. Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced or enhanced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Also disclosed are fusion polypeptides. A polypeptide may be a fusion polypeptide that comprises multiple polypeptides as described herein, or that comprises at least one polypeptide as described herein and an unrelated sequence, such as a known bacterial protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

As this specification discusses various polypeptides and polypeptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptides.

Disclosed herein are functional nucleic acids that can interact with the polynucleotides encoding the proteins disclosed herein, specifically the Rv proteins such as Rv0686, Rv2151c, Rv2240c, Rv3596c, and Rv3800c. Functional nucleic acids are nucleic acid molecules that have a specific function, such as binding a target molecule or agent or catalyzing a specific reaction. Functional nucleic acid molecules can be divided into the following categories, which are not meant to be limiting. For example, functional nucleic acids include antisense molecules, siRNA, shRNA, aptamers, ribozymes, triplex forming molecules, and external guide sequences. The functional nucleic acid molecules can act as effectors, inhibitors, modulators, and stimulators of a specific activity possessed by a target molecule or agent, or the functional nucleic acid molecules can possess a de novo activity independent of any other molecules.

Disclosed herein are expression vectors comprising polynucleotides corresponding to the proteins disclosed herein operably linked to a control element. Also disclosed herein are host cells transformed or transfected with an expression vector comprising the polynucleotides corresponding to the proteins disclosed herein. Also disclosed herein are methods of delivering the polynucleotides of the invention into cells. Also disclosed are host cells transformed or transfected with an expression vector.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be used to express those compositions disclosed herein useful for modulating the expression of Rv0686, Rv2151c, Rv2240c, Rv3596c, or Rv3800c, for example. Expression vectors can be used in eukaryotic host cells (yeast, fungi, insect, plant, animal, human or nucleated cells) and may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The disclosed vectors provide DNA molecules that are capable of integration into a mammalian chromosome without substantial toxicity.

The inserted nucleic acids in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

As used herein, the term antibodies includes both polyclonal and monoclonal antibodies. In addition to intact immunoglobulin molecules, also disclosed are antibody fragments or polymers of those immunoglobulin molecules, and human or humanized versions of immunoglobulin molecules or fragments thereof, as long as they are chosen for their ability to interact with the polypeptides disclosed herein.

As used herein, the term antibody fragments is intended to mean portions of a complete antibody. A complete antibody refers to an antibody having two complete light chains and two complete heavy chains. An antibody fragment lacks all or a portion of one or more of the chains. Antibody fragments for use in antibody conjugates can bind antigens. Preferably, the antibody fragment is specific for an antigen. An antibody or antibody fragment is specific for an antigen if it binds with significantly greater affinity to one epitope than to other epitopes. The antibodies or antibody fragments can be tested for their desired activity using the in vitro assays described herein, or by analogous methods, after which their in vivo therapeutic or prophylactic activities are tested according to known clinical testing methods.

As used herein, the term antibody or antibodies can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germline mutant mice results in complete inhibition of endogenous antibody production, and the successful transfer of the human germ-line antibody gene array into such germ-line mutant mice results in the production of human antibodies upon antigen challenge.

Disclosed herein are polynucleotide, polypeptide, antibody, T-cell, TCR, or APC compositions in pharmaceutically acceptable carriers for administration to a cell or a subject, either alone, or in combination with one or more other modalities of therapy. For example, disclosed herein is a composition comprising a physiologically acceptable carrier and a polypeptide as described herein. Such compositions can be administered in vivo. As used herein, the term pharmaceutically acceptable is meant to include material that is not biologically or otherwise undesirable, i.e., the material may be administered to a subject, along with the polypeptide, antibody, polynucleotide or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), intramuscularly, intraperitoneally, transdermally, extracorporeally, topically or by inhalant. Administration of the compositions by inhalant can be through the nose or mouth via delivery by a spraying or droplet mechanism.

The exact amount of the compositions required will vary from subject to subject, depending on the species, age, weight and general condition of the subject, the severity of disease being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated herein by reference in its entirety for fits teaching of an approach for parenteral administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Following administration of a disclosed composition, such as an antibody, for treating, inhibiting, or preventing a *Mycobacterium*-related disease, the efficacy of the therapeutic antibody can be assessed in various ways well known to the skilled practitioner. For instance, one of ordinary skill in the art will understand that a composition, such as an antibody, disclosed herein is efficacious in treating or inhibiting a *Mycobacterium*-related disease in a subject by observing that the composition reduces the symptoms or markers of the disease.

The compositions that inhibit *Mycobacterium*-related diseases disclosed herein may be administered prophylactically to subjects or subjects who are at risk for a *Mycobacterium*-related disease.

The disclosed compositions and methods can also be used for example as tools to isolate and test new drug candidates for a variety of *Mycobacterium*-related diseases.

In addition, the proteins described herein may be used as markers for the progression of *Mycobacterium* infection. The assays as described above for the diagnosis of *Mycobacterium* related diseases may be performed over time, and the change in the level of reactive polypeptide(s) or polynucleotide(s) evaluated. For example, the assays may be performed every 24-72 hours for a period of 6 months to 1 year, and thereafter performed as needed. In general, tuberculosis, for example, is progressing in those subjects in whom the level of polypeptide or polynucleotide detected increases over time. In addition, the compositions described herein may be used to monitor the level of antibodies specific for tuberculosis, for example.

As noted herein, to improve sensitivity, multiple bacterial proteins may be assayed within a given sample. Binding agents specific for different polypeptide or antibodies provided herein may be combined within a single assay. Further, multiple primers or probes may be used concurrently. The selection of bacterial polypeptides may be based on routine experiments to determine combinations that results in optimal sensitivity. In addition, or alternatively, assays for bacterial polypeptides or antibodies provided herein may be combined with assays for other known bacterial antigens such as Cfp-10 or Esat-6.

Also disclosed herein are kits that comprise at least one antibody to, or at least one polypeptide selected from, the group consisting of Rv0686, Rv2151c, Rv2240c, Rv3596c, and Rv3800c, optionally attached to a solid support or further comprising a means for attaching to a solid support. The kit can optionally comprise fragments of the antibody or polypeptide. The kit can optionally comprise an antibody that specifically recognizes Cfp-10 or an antibody that specifically recognizes Esat-6 or can comprise the polypeptides (Cfp-10 and/or Esat-6) or fragments thereof. Also disclosed is a kit that measures IFN-γ (or any other cytokine) in response to the presence of Cfp-10 and/or Esat-6 and any modification thereof by the Rv proteins disclosed herein.

The Rv proteins can be used in combination with commercial kits such as, the QuantiFERON®-TB test (QFT) or QuantiFERON-TB Gold test (QFT-G) (Cellestis Limited; Carnegie, Victoria, Australia) which can be used for detecting latent *Mycobacterium tuberculosis* infection. These tests are an in vitro diagnostic aid that measures a component of cell-mediated immune reactivity to *M. tuberculosis*. The tests are based on the quantification of interferon-gamma (IFN-γ) released from sensitized lymphocytes in whole blood incubated overnight with purified protein derivative (PPD) from *M. tuberculosis* and control antigens.

The proteins disclosed herein can also be used in conjunction with the tuberculin skin testing (TST), which has been used for years as an aid in diagnosing both active and latent tuberculosis infection and includes measurement of the delayed type hypersensitivity response 48-72 hours after intradermal injection of PPD.

The kits can include any reagent or combination of reagents discussed herein or that would be understood to be required or beneficial in the practice of the disclosed methods and a container or assay platform. For example, disclosed herein is a kit comprising at least one antibody that specifically binds to one or more of Rv0686, Rv2151c, Rv2240c, Rv3596c or Rv3800c. Also disclosed herein is a kit comprising one or more of Rv0686, Rv2151c, Rv2240c, Rv3596c, Rv3800c, or a variant or fragment thereof, wherein the polypeptide is attached to a solid support or wherein the kit contains a means for attaching to a solid support. The kit can comprise polypeptides or antibodies related to Cfp-10 or Esat-6.

Also disclosed are kits that comprise compounds, reagents, containers, or equipment. Reagents can include buffers to be used in the assay. Such kits may also, or alternatively, contain a detection reagent that contains a reporter group suitable for direct or indirect detection. Optionally, a kit may be designed to detect the level of mRNA encoding a bacterial polypeptide in a biological sample. Such kits generally comprise at least one oligonucleotide probe or primer, as described above, that hybridizes to a polynucleotide encoding a bacterial polypeptide. Such an oligonucleotide may be used, for example, within a PCR or hybridization assay. Additional components that may be present within such kits include a second oligonucleotide or a diagnostic reagent or container to facilitate the detection of a polynucleotide encoding a bacterial protein.

Optionally, a kit may be designed to detect the level of antibodies specific for a bacterial protein in a biological sample.

Also disclosed herein is the M-PFC system, a system for studying protein-protein association in mycobacteria. This system has been developed to allow for the study of Mtb virulence mechanisms and other functional pathways through protein-protein association. In this approach, the independent genetic coupling of an enzyme reporter, such as mDHFR complementary fragments ([F1,2] and [F3]), with two mycobacterial interacting proteins leads to the reconstitution of the enzyme reporter activity, in this example, mDHFR activity, in vivo, at a concentration where endogenous mycobacterial DHFR activity is inhibited. The readout of this complementation event is the in vivo reconstitution of mDHFR fragments F[1,2] and F[3] that allow for the selection of mycobacterial clones resistant to TRIM. Importantly, only when F[1,2] and F[3] are fused with two interacting proteins, will heterodimerization results in reconstitution of mDHFR. An important advantage of studying protein association in mycobacteria rather than surrogate hosts such as yeast and E. coli is that appropriate modifications (e.g., phosphorylation), cofactors, and the exclusive intracellular environments unique to the natural host, can modulate the outcome of interactions.

mDHFR is a small 21 kDa monomeric protein that contains three structural fragments (F[1], F[2] and F[3]) containing two domains; an adenine-binding domain (F[2]) and a discontinuous domain (F[1] and F[3]). This property can be exploited to form the M-PFC system. The M-PFC system dissects protein-protein association in vivo using the model organism *Mycobacterium smegmatis* (Msm) as host. The strategy is based on the fact that if two mycobacterial interacting proteins A and B are independently fused to the mDHFR complementary fragments F[1,2] and F[3], respectively, and co-transformed into mycobacteria, in vivo association of AF[1,2] and BF[3] will facilitate the functional reassembly of the fragments into active mDHFR enzyme. The addition of small tags (F[1,2], 105 aa and F[3], 80 aa) to interacting proteins only minimally effects protein-protein association. Despite the fact that prokaryotic and eukaryotic DHFRs are targets of the anti-folate drug TRIM, mammalian DHFR has a ~12,000 fold lower affinity for TRIM than does bacterial DHFR. This selective targeting of mycobacterial DHFR's by TRIM is the basis of the M-PFC system and allows for the screening of the growth of recombinant mycobacteria expressing mDHFR in the presence of TRIM concentrations that inhibits endogenous Msm DHFR (as illustrated in FIG. 1). Mycobacterial cells expressing complementary fragments of mDHFR fused to interacting proteins can survive in medium containing TRIM. Msm was chosen as a host for the M-PFC experiments, because this strain is sensitive to TRIM (~40 μg/ml on 7H11) and is a non-pathogenic, rapid grower that was shown to be an excellent surrogate host for studying Mtb gene regulation and secretion.

As shown in FIG. 1, interacting proteins A and B are fused to complementary mDHFR fragments F[1,2] and F[3]. Co-transformation of the A-F[1,2] and B-F[3] fusions in Msm results in the functional reconstitution of mDHFR activity and subsequent growth on TRIM plates whereas proteins that do not interact (A and C), do not reconstitute F[1,2] and F[3] and do not allow transformants to survive on TRIM plates.

Virulence pathways are mediated by complex networks of molecular interactions, which upon disruption, alter protein-protein associations. Thus, protein-protein interactions show a direct link or role, whereas gene disruption experiments are an indirect measure.

M-PFC enables the shedding of light on the mechanism of protein secretion in Mtb and identified several novel components of the Cfp-10 secretory pathway. M-PFC has successfully been implemented for studying protein-protein association in mycobacteria. Several known protein-protein interactions in Msm were studied, and an assay was developed to visualize and quantify the strength of interaction (Example 1). M-PFC has been tested and validated by screening an Mtb library of proteins that associate with Cfp-10. The M-PFC system has the ability to identify and characterize novel virulence pathways involved in persistence and pathogenesis of Mtb.

Further disclosed is an assay for detection of molecular interactions in *Mycobacterium* comprising a reassembly of separate fragments of an enzyme wherein reassembly of the enzyme fragments is operated by the interaction of molecular domains fused to each enzyme fragment, wherein reassembly of the enzyme fragments is independent of other molecular processes and wherein said reassembly is detected by means of reconstitution of activity of said enzyme. The *Mycobacterium* can be *M. smegmatis, M. tuberculosis*, or *M. avium*, for example.

Also disclosed is a method for detecting biomolecular interactions in *Mycobacterium*, said method comprising detecting the association between a first fusion protein comprising a fragment of an enzyme reporter molecule and a first polypeptide, and a second fusion protein comprising a different fragment of the enzyme reporter molecule and a second polypeptide in a *Mycobacterium* cell, wherein association of the fusion proteins results in reassembly of the enzyme reporter molecule and reconstitution of enzyme reporter activity, and wherein the biomolecular interaction between the first and the second polypeptide is measured by detecting the activity of the enzyme reporter molecule.

Also disclosed is a method comprising an assay in *Mycobacterium* wherein fragments of a first enzyme molecule are fused to a second molecule and fragment association is detected by reconstitution of the first enzyme molecule's activity.

Also disclosed is a method of screening a DNA library of *Mycobacterium* peptides for peptides that interact with a *Mycobacterium* polypeptide, comprising performing an enzyme complementation assay wherein the interaction between a peptide from the DNA library and the *Mycobacterium* polypeptide is detected by reconstitution of enzyme activity.

Disclosed herein is a method of identifying an agent that modulates interaction between Cfp-10 and Rv0686, Rv2151c, Rv2240c, Rv3596c, Rv3800c, or a variant or fragment thereof comprising contacting a *Mycobacterium* cell that expresses a first fusion protein comprising a fragment of an enzyme reporter molecule fused to Cfp-10 and a second fusion protein comprising a second fragment of an enzyme reporter molecule fused to one of Rv0686, Rv2151c, Rv2240c, Rv3596c, Rv3800c, or a variant or fragment thereof, with the agent, under conditions where the first and the second fusion protein normally associate to reconstitute enzyme report molecule activity in the absence of the agent; and detecting a change in the activity of the enzyme reporter molecule. A change in the activity of the enzyme reporter molecule indicates that the agent is an agent that modulates the interaction between Cfp-10 and Rv0686, Rv2151c, Rv2240c, Rv3596c, Rv3800c, or a variant or fragment thereof.

Disclosed is a method of identifying an agent that modulates interaction between Esat-6 and Rv0686, Rv2151c, Rv2240c, Rv3596c, Rv3800c, or a variant or fragment thereof comprising contacting a *Mycobacterium* cell that expresses a first fusion protein comprising a fragment of an enzyme reporter molecule fused to Esat-6 and a second fusion protein comprising a second fragment of an enzyme reporter molecule fused to one of Rv0686, Rv2151c, Rv2240c, Rv3596c, Rv3800c or a fragment thereof, with the agent, under conditions where the first and the second fusion protein normally associate to reconstitute enzyme report molecule activity in the absence of the agent; and detecting a change in the activity of the enzyme reporter molecule, wherein a change in the activity of the enzyme reporter molecule indicates that the agent is an agent that modulates the interaction between Esat-6 and Rv0686, Rv2151c, Rv2240c, Rv3596c, Rv3800c, or a variant or fragment thereof.

In the above examples, the enzyme can be murine dihydrofolate reductase (mDHFR). By way of non-limiting example, the *Mycobacterium* can be *M. smegmatis, M. tuberculosis, M. bovis, M. bovis* BCG, *M. marinum* or *M. avium.*

Therefore, disclosed herein is a strategy for detecting interactions in *Mycobacterium* with other molecules including other proteins, nucleic acids, carbohydrates or for screening small molecule libraries for compounds of potential therapeutic value. In a preferred embodiment, the instant invention seeks to provide an oligomerization-assisted complementation of fragments of monomeric enzymes that require no other proteins for the detection of their activity. In one such embodiment, a protein-fragment complementation assay (PCA) based on reconstitution of dihydrofolate reductase activity by complementation of defined fragments of the enzyme in *E. coli* is hereby provided. This assay requires no additional endogenous factors for detecting specific protein-protein interactions (i.e. leucine zipper interactions) and can be conveniently extended to screening cDNA, nucleic acid, small molecule or protein design libraries for molecular interactions. In addition, the assay can also be adapted for detection of protein interactions in any cellular context or compartment and be used to distinguish between induced versus constitutive protein interactions.

One particular strategy for designing a protein complementation assay (PCA) is based on using the following characteristics: 1) A protein or enzyme that is relatively small and monomeric, 2) for which there is a large literature of structural and functional information, 3) for which simple assays exist for the reconstitution of the protein or activity of the enzyme, both in vivo and in vitro, and 4) for which overexpression in eukaryotic and prokaryotic cells has been demonstrated. If these criteria are met, the structure of the enzyme is used to decide the best position in the polypeptide chain to split the gene in two, based on the following criteria: 1) the fragments should result in subdomains of continuous polypeptide; that is, the resulting fragments will not disrupt the subdomain structure of the protein, 2) the catalytic and cofactor binding sites should all be contained in one fragment, and 3) resulting new N- and C-termini should be on the same face of the protein to avoid the need for long peptide linkers and allow for studies of orientation-dependence of protein binding.

The above mentioned criteria do not all need to be satisfied for a proper working assay method. It is an advantage that the enzyme be small, preferably between 10-40 kDa. Although monomeric enzymes are preferred, multimeric enzymes can also be envisaged as within the scope of the present invention. The dimeric protein tyrosinase can be used in the instant assay. The information on the structure of the enzyme provides an additional advantage in designing the PCA, but is not necessary. Indeed, an additional strategy, to develop PCAs is presented, based on a combination of exonuclease digestion-generated protein fragments followed by directed protein evolution in application to the enzyme aminoglycoside kinase. Although the overexpression in prokaryotic cells is preferred it is not a necessity. The enzyme catalytic site (of the chosen enzyme) does not absolutely need to be on same molecule.

The present application explains the rationale and criteria for using a particular enzyme in a PCA. The gene for a protein or enzyme is rationally dissected into two or more fragments. Using molecular biology techniques, the chosen fragments are subcloned, and to the 5' ends (or 3 ends) of each, proteins that either are known or thought to interact are fused. Co-transfection or transformation these DNA constructs into cells is then carried out. Reassembly of the probe protein or enzyme from its fragments is catalyzed by the binding of the test proteins to each other, and reconstitution is observed with some assay. These assays work when the fused, interacting proteins catalyze the reassembly of the enzyme. That is, observation of reconstituted enzyme activity is a measure of the interaction of the fused proteins.

The methods disclosed herein focus on a PCA based on the enzyme dihydrofolate reductase. Additional assays, including those based on enzymes that can act as dominant or recessive drug selection or metabolic salvage pathways, are disclosed. In addition, PCAs based on enzymes that will produce a colored or fluorescent product are also disclosed. As discussed herein, the PCA strategy can be both generalized and automated for functional testing of novel genes, screening of natural products or compound libraries for pharmacological activity and identification of novel gene products that interact with DNA, RNA or carbohydrates are disclosed. The PCA strategy can also be applied to identifying natural products or small molecules from compound libraries of potential therapeutic value that can inhibit or activate such molecular interactions and how enzyme substrates and small molecule inhibitors of enzymes can be identified. Finally, the PCA strategy can be used to perform protein engineering experiments that could lead to designed enzymes with industrial applications or peptides with biological activity.

The methods disclosed herein are not intended to be limited to DHFR or the other PCAs presented, rather, these are only examples of non-limiting embodiments of the protein *Mycobacterium* complementation assay. Moreover, the PCAs are not intended to be limited in the context in which they can be used. Rather constructs can be designed for targeting the PCA fusions to specific compartments in the cell by addition of signaling peptide sequences. Further, induced versus constitutive protein-protein interactions can be distinguished by a eukaryotic version of the PCA, in the case of an interaction that is triggered by a biochemical event. Also, the system can be adapted for use in screening for novel, induced protein-molecular associations between a target protein and an expression library.

Additionally described herein is a system and method for detecting biomolecular interactions in Mycobacterium using the M-PFC system that can be used to screen drug candidates (agents) for activity a method for identifying an agent (target) in a Mycobacterial cell that interacts with a polypeptide involved the steps of combining a first fusion protein comprising a first fragment of an enzyme reporter molecule and a first polypeptide, a second fusion protein comprising a second fragment of the enzyme reporter molecule and a second polypeptide, and a binding molecule cross linked to a target molecule, wherein the binding molecule associates with the first polypeptide and association of the target molecule with the second polypeptide results in reassembly of the enzyme reporter molecule and reconstitution of the enzyme reporter activity; and detecting the enzyme reporter activity. A change in the activity of the reporter molecule indicates that the target is interacting with the second polypeptide. The target molecule can be directly linked to the binding molecule by a covalent bond between the two or a linkage molecule can be used to link the target molecule to the binding molecule.

Figure 2:
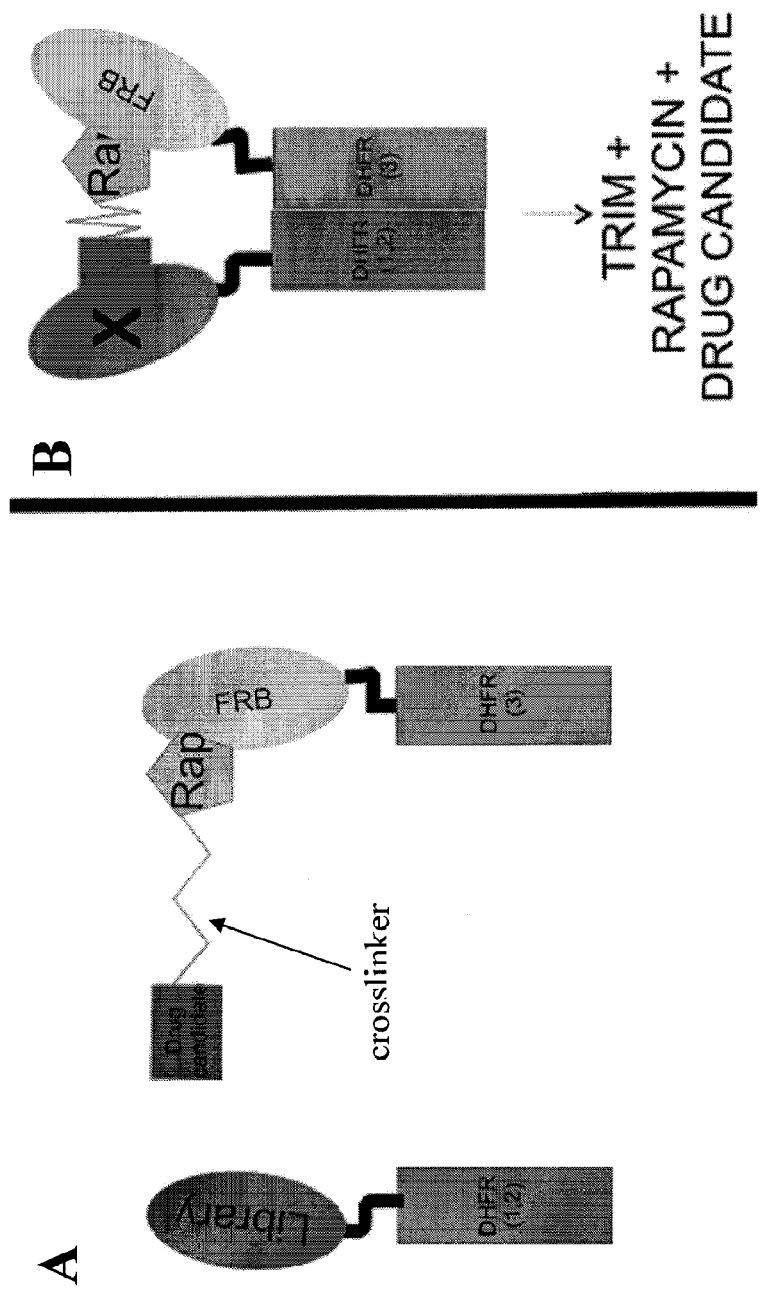
FIGS. 2A and 2B generally illustrate the steps in a method for identifying a polypeptide:agent interaction.
Figure 3:
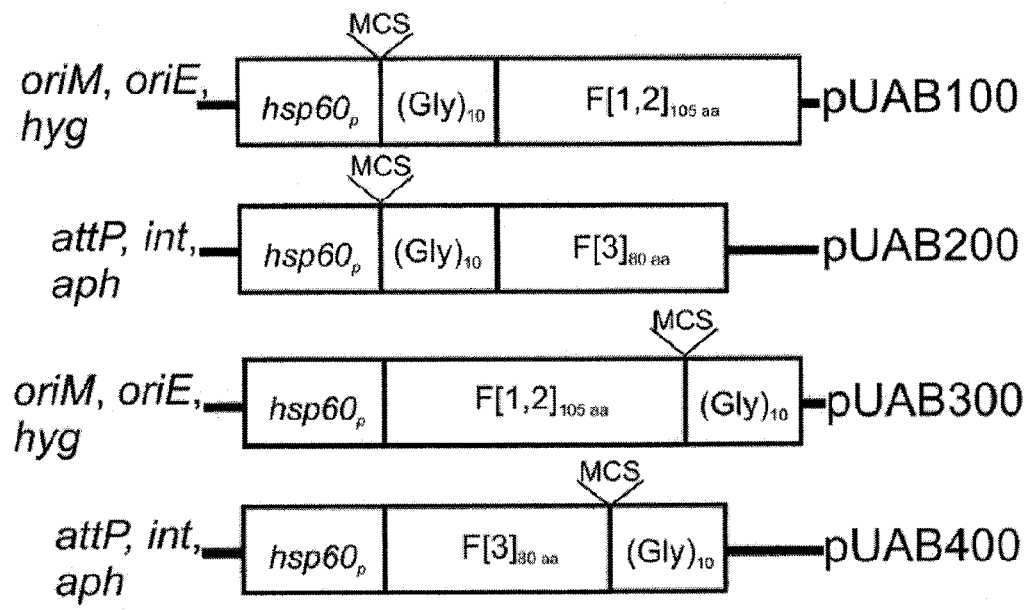
FIG. 3 shows a schematic diagram of the plasmids used in M-PFC.

FIGS. 2A and 2B illustrate one embodiment of this method schematically. The first fusion protein is shown in FIG. 2A as the FRB-DFHR[3] combination, in which FRB is a polypeptide with known affinity to rapamycin and DHFR[3] is the first fragment of the enzyme reporter molecule. The second fusion protein is shown in FIG. 2A as the Library-DFHR[1,2] combination, in which Library is the polypeptide and DFHR [1,2] is the second fragment of the enzyme reporter molecule. The binding molecule cross linked to a target molecule is shown in FIG. 2A as [Drug Candidate]-crosslinker-[Rap], in which "Drug Candidate" is the target molecule and "Rap" is rapamycin. In the system shown in FIG. 2, because FRB has an affinity for rapamycin, the target ("Drug Candidate") will be associated with the FRB containing fusion protein. If a fusion protein containing a polypeptide with affinity for the target ("Drug Candidate") is present, the fusion protein will form a complex with a FRB containing fusion protein. This fusion protein:fusion protein complex mediated by the binding molecule cross linked to a target molecule (as shown in FIG. 2B) will have reconstituted reporter molecule activity. The reconstituted DFHR reporter activity will allow cells containing a selected target molecule to grow in the presence of trimethoprim.

Reporter enzyme activity can be detected by multiple systems that will be known to those of skill in the art, such as, but not limited to, spectrophotometry, fluorescence, enzymatic activity, spectrometry, or visual means.

Choices of polypeptides that have affinity to a chosen binding molecule can vary depending on the system being investigated and on other factors that will be readily apparent to those of skill in the art. For example, when rapamycin is used as the binding molecule, polypeptides such as FRB and FKBP12 which have affinity for rapamycin (see Example 3) can be used. The polypeptides of the fusion proteins can also be Mycobacterial polypeptides.

A wide variety of crosslinkers are available and the choice of a crosslinker may depend on the screen to be performed. The linkage may be formed by any of the methods known in the art (March, J., Advanced Organic Chemistry (1985) pub. John Wiley & Sons Inc.; House, H. H., Modern Synthetic Reactions (1972) pub. Benjamin Cummings). Descriptions of linkage chemistries are also provided by U.S. Pat. No. 7,083, 918, US 2004/0106154, US 2002/0168685, WO 94/18317, WO 95/02684, WO 96/13613, WO96/06097, and WO 01/53355 (incorporated herein by reference in their entireties at least for the compounds and methods taught herein). Molecules capable of acting as a linkage ("linkers") are commercially available or can be easily prepared. Linkers are available or can be prepared that vary in hydrophobicity, length, and flexibility.

Linkers are available (or can be designed) that respond to enzymatic activity. For example, a linker can contain a glycosidase bond, which may be cleaved by a glycosidase enzyme and formed by a glycosyltransferase enzyme. Other examples of linker components with enzyme activity include amide bonds, which may be cleaved by a protease and formed by peptidase or transpeptidase; aldol product bonds, which are cleaved by a retro-aldolase and formed by aldolase; ester bonds; and phosphodiester bonds. These types of linkers can be used in bacterial based screens (similar to their use in yeast based screens, which are described in WO 01/53355). Other enzymatically active linker components and their respective enzymes are intended to be within the scope of this disclosure.

Compound libraries for screening can be compiled or synthesized, and such libraries can be generated or purchased from commercial sources. Such libraries can contain a known set of molecules, in the case of a compiled (or fully characterized) library or an unknown set of molecules such as from a combinatorially produced library.

Also disclosed herein are kits comprising a first fusion protein comprising a polypeptide with affinity for a binding molecule. Such kits can further comprise one or more of a first enzyme reporter fragment, a binding molecule with an attached crosslinker, and a second enzyme reporter fragment. Such kits can further comprise compounds, reagents or combinations of reagents, containers or equipment that would be understood to be required or beneficial in the practice of the disclosed methods and a container or assay platform. Reagents can include buffers to be used in the assay. These kits can also include solid supports such as multiwell plates or a mobile support such as beads. The kits can further include instructions.

Further described herein are methods of reducing Mycobacterium virulence, reducing Rv3133c dimerization in Mycobacterium, and treating a subject with a Mycobacterium infection using compounds identified using the M-PFC system.

Using the M-PFC system, as described above compounds have been identified that reduce and/or inhibit Rv3133c (also known as DosR and DevR) dimerization interactions in Mycobacterium. These compounds include those having the following general formula:

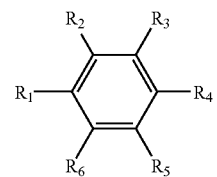

wherein:

$R_1$ is NH—X or C(=O)—X, wherein X is a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl;

$R_4$ is OH; $SO_2$—Y, wherein Y is a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl; or $SO_2$—NH—Z, wherein Z is a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl; and each of $R_2$, $R_3$, $R_5$, and $R_6$ is independently H, OH, a substituted or unsubstituted $C_1$-$C_{12}$ alkyl, substituted or unsubstituted $C_1$-$C_{12}$ alkenyl, substituted or unsubstituted $C_1$-$C_{12}$ alkynyl, or substituted or unsubstituted aryl.

Alkyl groups useful in the compounds described herein have from 1 to about 12 carbon atoms, 1 to about 8 carbon atoms, 1 to about 6 carbon atoms, or 1, 2, 3, or 4 carbon atoms. Methyl, ethyl, propyl, and isopropyl groups are examples of alkyl groups that can be used in the compounds. The term alkyl, unless otherwise modified, refers to cyclic, noncyclic, and hybrid cyclic/nonyclic groups. Noncyclic groups include straight chain and branched groups. Cyclic groups include groups with one or more substitutions. Hybrid cyclic/noncyclic groups include a cyclic portion and a non-cyclic portion such as, for example, methylcyclohexane, ethylcyclohexane, and propylcyclohexane.

Alkenyl and alkynyl groups useful in the compounds described herein have one or more unsaturated linkages and from 2 to about 12 carbon atoms, 2 to about 8 carbon atoms, 2 to about 6 carbon atoms, or 2, 3, or 4 carbon atoms. The terms alkenyl and alkynyl, unless otherwise modified, refer to both cyclic, noncyclic, and hybrid cyclic/noncyclic groups. Noncyclic groups include straight chain and branched groups. Cyclic groups include groups with one or more substitutions. Hybrid cyclic/noncyclic groups include a cyclic portion and a non-cyclic portion.

Alkoxy groups useful in the compounds described herein include groups having one or more oxygen linkages and from 1 to about 12 carbon atoms, 1 to about 8 carbon atoms, 1 to about 6 carbon atoms, or 1, 2, 3, or 4 carbon atoms.

Aminoalkyl groups useful in the compounds described herein include groups having one or more primary, secondary, and/or tertiary amine groups and from about 1 to about 12 carbon atoms, 1 to about 8 carbon atoms, 1 to about 6 carbon atoms, or 1, 2, 3, or 4 carbon atoms.

Alkylthio groups useful in the compounds described herein have one or more thioether linkages and from 1 to about 12 carbon atoms, 1 to about 8 carbon atoms, 1 to about 6 carbon atoms, or 2, 3, or 4 carbon atoms.

Alkylsulfonyl groups useful in the compounds described herein include those groups having one or more sulfonyl ($SO_2$) groups and from 1 to about 12 carbon atoms, 1 to about 8 carbon atoms, 1 to about 6 carbon atoms or 1, 2, 3, or 4 carbon atoms.

Heteroaromatic groups useful in the compounds described herein contain one, two or three heteroatoms selected from N, O, or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl, and benzothiazolyl. Suitable heteroalicyclic groups contain one, two or three heteroatoms selected from N, O, or S atoms and include, e.g., tetrahydrofuranyl, tetrahydropyranyl, piperidinyl, morpholino and pyrrolindinyl groups.

Suitable carbocyclic aryl groups useful in the compounds described herein include single and multiple ring compounds, as well as multiple ring compounds that contain separate and/or fused aryl groups. Useful carbocyclic aryl groups, for example, contain 1 to 3 separate or fused rings and from 6 to about 18 carbon ring atoms. Examples of carbocyclic aryl groups include phenyl groups, napthyl groups (including 1-naphthyl and 2-naphthyl), biphenyl groups, phenanthryl groups, and anthracyl groups. Examples of phenyl groups include substituted phenyls such as 2-substituted phenyl, 3-substituted phenyl, 2,3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl, and the like.

References to substituted groups in the compounds described herein refer to groups that have one or more additional moieties that are attached at one or more available positions of the substituted group. Examples of such additional moieties that can be added to a group include halogens such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, 1 to about 6 carbon atoms, or 1 to about 3 carbon atoms; alkenyl and alkynyl groups including groups having one or more unsaturated linkages and from 2 to about 12 carbon, 2 to about 6 carbon atoms, or 2 to about 4 carbon atoms; oxygen, e.g., the formation of a carbonyl on the substituted group or the addition of a hydroxyl group; alkoxy groups having one or more oxygen linkages and from 1 to about 12 carbon atoms, or 1 to about 6 carbon atoms; aryloxy such as phenoxy; alkylthio groups including those moieties having one or more thioether linkages and from 1 to about 12 carbon atoms, or 1 to about 6 carbon atoms; alkylsulfinyl groups including those moieties having one or more sulfinyl linkages and from 1 to about 12 carbon atoms, or 1 to about 6 carbon atoms; alkylsulfonyl groups including those moieties having one or more sulfonyl linkages and from 1 to about 12 carbon atoms, or 1 to about 6 carbon atoms; aminoalkyl groups such as groups having one or more nitrogen atoms and from 1 to about 12 carbon atoms, or 1 to about 6 carbon atoms; carbocylic aryl having 6 or more carbons, e.g., phenyl or biphenyl; aralkyl groups such as benzyl; and nitrile groups. Additionally, substituent groups may themselves be substituted, as in a trifluoromethylcinnamoyl group or an aminoacid acyl group such as with valine or Boc-valine. Further, multiple substitutions can occur in a single group, for example, a cycloalkyl group can have one or more oxygen linkages and one or more thioether linkages Additional moieties available for substitution of a substituted group include modified and unmodified imidazole and imidazole analog groups. Imidazoles are heterocyclic aromatic organic compounds with the following formula:

The ring of an imidazole group can be substituted to create imidazole analog groups. Examples of imidazole analog groups include benzimidazole and modified benzimidazole groups. Benzimidazoles have the following general structure:

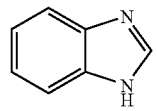

Benzimidazoles can be substituted as discussed above. Benzimidazoles can also be modified, for example, by replacing one of the imidazole ring nitrogens with an oxygen. An example of a modified benzimidazole includes benzooxazole. Benzooxazole has the following structure:

An example of a substituted benzimidazole includes 1-methyl-1,3-dihydro-benzoimidazol-2-ylideneamine. 1-methyl-1,3-dihydro-benzoimidazol-2-ylideneamine has the following structure:

When used as substitution moieties, benzimidazoles and benzimidazole analogs can be linked to the substituted group, for example, through the open carbon on the imidazole ring or through one of the imidazole ring nitrogens.

Further examples of compounds that reduce and/or inhibit Rv3133c dimerization interactions in *Mycobacterium* include N-(4-[(acetylamino)sulfonyl]phenyl)-3-phenylpropanamide; 1-(3,5-di-tert-butyl-4-hydroxyphenyl)-2-(2-imino-3-methyl-2,3-dihydro-1H-benzimidazol-1-yl)ethanone hydrochloride; and 1-(1,3-benzoxazol-2-yl)-3-({4-[(2-hydroxyethyl)sulfonyl]phenyl}amino)acrylaldehyde.

N-(4-[(acetylamino)sulfonyl]phenyl)-3-phenylpropanamide has the following structure:

1-(3,5-di-tert-butyl-4-hydroxyphenyl)-2-(2-imino-3-methyl-2,3-dihydro-1H-benzimidazol-1yl)ethanone hydrochloride has the following structure:

2-(1,3-benzoxazol-2-yl)-3-({4-[(2-hydroxyethyl)sulfonyl]phenyl}amino)acrylaldehyde has the following structure:

The compounds described herein can be provided in a pharmaceutically acceptable form including pharmaceutically acceptable salts and derivatives thereof. These compositions can include pharmaceutically acceptable carriers or stabilizers. The term pharmaceutically acceptable acid salts and derivatives refers to salts and derivatives of the compounds described herein that retain the biological effectiveness and properties of the compounds as described, and that are not biologically or otherwise undesirable. Pharmaceutically acceptable salts can be formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Methods of using the compounds described herein include methods of reducing Mycobacterial virulence, methods of reducing RV3133c dimerization, and methods of treating a subject with a Mycobacterial infection.

The methods of reducing Mycobacterial virulence comprise contacting a *Mycobacterium* with a compound as described herein, wherein the compound reduces virulence as compared to the virulence of *Mycobacterium* in the absence of the compound.

The methods of reducing RV3133c dimerization comprise contacting a *Mycobacterium* with a compound as described herein, wherein the compound reduces Rv3133c dimerization as compared to Rv3133c dimerization in *Mycobacterium* in the absence of the compound.

The methods of treating a subject with a Mycobacterial infection comprise administering to the subject a compound as described here in a pharmaceutically acceptable form, wherein the compound reduces one or more symptoms of the *Mycobacterium* infection as compared to the absence of the compound. Symptoms can include, for example, cough, fatigue, shortness of breath, weight loss, fever, and chest pain.

Also disclosed herein are kits for reducing Mycobacterial virulence, reducing RV3133c dimerization, and treating a subject with a Mycobacterial infection. These kits comprise one or more of the compounds described herein, optionally with a solid support such as a multiwell plate of a mobile support such as beads. Such kits can further comprise compounds, reagents or combinations of reagents, containers or equipment that would be understood to be required or beneficial in the practice of the disclosed methods and a container or assay platform. Reagents can include buffers to be used in the assay. The kits can further include instructions.

The examples below are intended to further illustrate certain embodiments of the invention, and are not intended to limit the scope of the claims.

EXAMPLES

Example 1

**Dissecting Virulence Pathways of *Mycobacterium tuberculosis* Through Protein-Protein Association**

Figure 4:
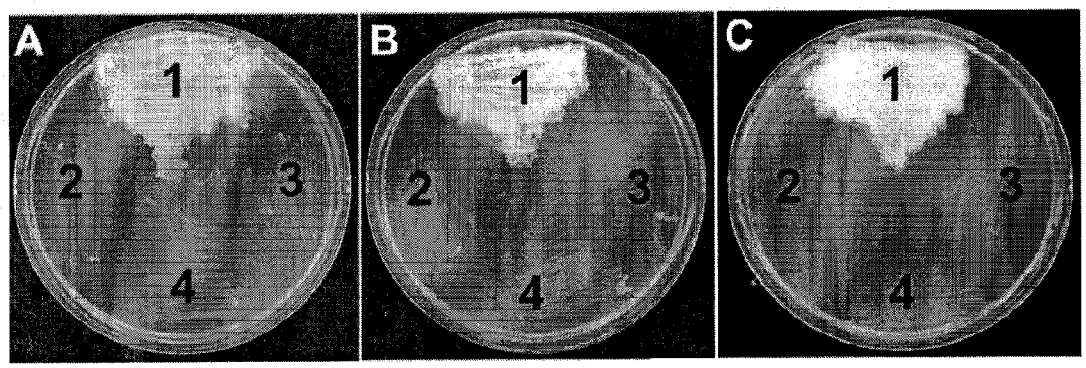
FIG. 4A shows cell culture results demonstrating that M-PFC can be used to show protein-protein association between GCN4 proteins: (1) $GCN4_{[F1,2]}/GCN4_{[F3]}$, (2) $GCN4_{[F1,2]}/hsp60_{[F3]}$, (3) $GCN4_{[F3]}/hsp60_{[F1,2]}$ (4) $hsp60_{[F1,2]}/hsp60_{[F3]}$.
FIG. 4B shows cell culture results demonstrating that M-PFC can be used to show protein-protein association between LdpD and KpdE proteins: (1) $KdpD_{[F1,2]}/KdpE_{[F3]}$, (2) $KdpD_{[F1,2]}/hsp60_{[F3]}$, (3) $KdpE_{[F3]}/hsp60_{[F1,2]}$ (4) $hsp60_{[F1,2]}/hsp60_{[F3]}$.
FIG. 4C shows cell culture results demonstrating that M-PFC can be used to show protein-protein association between Esat6 and Cfp-10 proteins: (1) $Esat-6_{[F1,2]}/Cfp-10_{[F3]}$, (2) $Esat-6_{[F1,2]}/hsp60_{[F3]}$, (3) $Cfp-10_{[F3]}/hsp60_{[F1,2]}$ (4) $hsp60_{[F1,2]}/hsp60_{[F3]}$.

The M-PFC system was used to study protein association in mycobacteria. *E. coli*-mycobacterial shuttle vectors, pUAB100 and pUAB200 (FIG. 2) were constructed to generate M-PFC fusion proteins. Previously, the mDHFR fragments were engineered such that the interacting protein pairs and F[1,2] and F[3] were separated by a flexible glycine linker peptide of 10 amino acids (Pelletier, J. N., Campbell-Valois, F. X. & Michnick, S. W. (1998) *Proc Natl Acad Sci USA* 95, 12141-6) thereby allowing the study of interactions across distances of 80 Å, designed to span the hydrodynamic radius of nearly all proteins (Cody, V., Luft, J. R., Ciszak, E., Kalman, T. I. & Freisheim, J. H. (1992) *Anticancer Drug Des* 7, 483-91). To demonstrate the feasibility of M-PFC to detect a diverse range of protein-protein associations in Msm, several well-characterized interacting partners namely, *Saccharomyces cerevisiae* GCN4 (Pelletier et al. (1998) *Proc Natl Acad Sci USA* 95, 12141-6), Mtb two-component proteins KdpD (Rv1028c)/KdpE (Rv1027c) (Steyn et al. (2003) *Mol Microbiol* 47, 1075-89) and Mtb secreted antigens Esat-6 (Rv3875)/Cfp-10 (Rv3874) (Renshaw et al. (2002) *J Biol Chem* 277, 21598-603) were selected. These bait and prey plasmids were generated as C-terminus fusions with the complementary fragments of mDHFR to generate the interacting protein pairs $GCN4_{[F1,2]}/GCN4_{[F3]}$, $KdpD_{[F1,2]}/KdpE_{[F3]}$ and $Esat-6_{[F1,2]}/Cfp-10_{[F3]}$. The complete open reading frames (ORF) were cloned into pUAB100 and pUAB200 under the control of a constitutive mycobacterial promoter (hsp60) as described in Material and Methods. Plasmids encoding interacting protein pairs fused independently to mDHFR fragments F[1,2] and F[3] were co-transformed into Msm and selected on 7H11/KAN/HYG. Transformants were sub-cultured onto 7H11KAN/HYG plates containing 50 μg/ml TRIM (7H11KAN/HYG/TRIM) and incubated at 37° C. for 3-6 days (FIG. 4). Growth was observed in all cases, showing that $GCN4_{[F1,2]}/GCN4_{[F3]}$, $KdpD_{[F1,2]}/KdpE_{[F3]}$ and $Esat-6_{[F1,2]}/Cfp-10_{[F3]}$ associate in Msm. Importantly, the control clones encoding only one protein ($GCN4_{[F1,2]}$, or $KdpD_{[F1,2]}$, or $Esat-6_{[F1,2]}$) fused to F[1,2] and a empty plasmid producing only F[3], showed no growth on TRIM plates. Furthermore, pairing clones with unrelated proteins, (e.g., Esat6 and KdpD) or swapping F[1,2] or F[3] indicate that association of [F1,2] and [F3] does not occur spontaneously, and that only interacting domains independently fused to both mDHFR fragments reconstitute [F1,2] and F[3]. The M-PFC system is thus capable of specifically detecting protein-protein associations in Msm. Since growth was detected in a relative short period (3-4 days), M-PCF is robust enough to detect a broad range of interactions.

Figure 5:
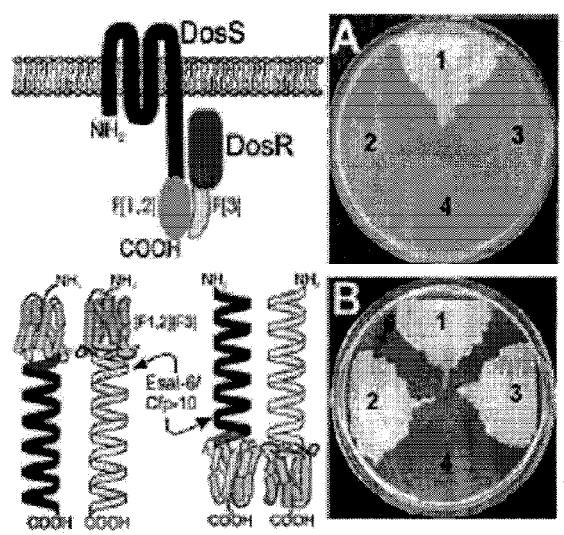
FIG. 5A shows an illustration of the DosS/DosR (which are also called DevS/DevR) interaction at a lipid bilayer (left) and a 7H11/HYG/KAN/TRIM cell culture (right) indicating that $DevR_{F[3]}$ and $DevS_{F[1,2]}$ associate, but that other fusion protein combinations do not associate: (1) $DevR_{F[3]}$ and $DevS_{F[1,2]}$, (2) $DevR_{F[3]}$ and $hsp60_{F[1,2]}$ (3) $hsp60_{F[3]}$ and $DevS_{F[1,2]}$, and (4) $hsp60_{F[1,2]}/hsp60_{F[3]}$.
FIG. 5B shows an illustration of both C- and N-terminal fusion proteins of Esat-6 and Cfp-10 with [F1,2] and [F3] (left) and a 7H11/HYG/KAN/TRIM cell culture (right) indicating that $Esat-6_{F[1,2]}/Cfp-10_{F[3]}$, and $_{F[1,2]}Esat-6_{F[3]}Cfp- 10 showed robust growth: (1) Esat-6F$_{[1,2]}$/Cfp-10$_{F[3]}$, (2) $_{F[1,2]}$Esat-6$_{F[3]}$Cfp-10, (3) GCN4$_{[F1,2]}$/GCN4$_{[F3]}$, and (4) hsp60$_{[F1,2]}$/hsp60$_{[F3]}$.

It is widely known that protein association and folding are modulated differently in the prokaryotic cytoplasm and membrane. In order to assess whether M-PFC is capable of detecting interactions between Mtb cytosolic and membrane signaling proteins, the interaction between the Mtb membrane-spanning sensor histidine kinase, DevS (Rv3132c) and its corresponding response regulator DevR (Rv3133c), (FIG. 5A) was studied. The Mtb DevR/DevS proteins comprise a two-component signaling system that has been shown to be required for reprogramming of the Mtb genetic response to hypoxia and nitric oxide, two environmental cues that can contribute to latency in vivo (Roberts et al. (2004) *J Biol Chem* 279, 23082-7; Park et al. (2003) *Mol Microbiol* 48, 833-43). The Mtb devR and devS ORFs were cloned into pUAB100 and pUAB200 to generate C-terminus fusions with F[3] and F[1,2] respectively, producing $DevR_{F[3]}$ and $DevS_{F[1,2]}$. Co-transformation of plasmids encoding $DevR_{F[3]}$ and $DevS_{F[1,2]}$ into Msm, and subsequent growth of transformants on 7H11/KAN/HYG/TRIM, demonstrated that association between $DevR_{F[1,2]}$ and $DevS_{F[3]}$ functionally reconstitute F[1,2] and F[3], thereby resulting in Msm resistance to TRIM (FIG. 5A). In contrast, clones containing empty control plasmids, or unrelated proteins (e.g KdpE) showed no growth on 7H11/KAN/HYG/TRIM plates, showing that the interaction is specific. Since clones producing $DevR_{F[3]}$ and $DeVS_{F[1,2]}$ grew slightly slower on 7H11/KAN/HYG/TRIM compared to clones producing $KdpD_{F[3]}/KdpE_{F[1,2]}$, and $Esat-6_{F[3]}/Cfp-10_{F[1,2]}$, the data show that the $DevR_{F[3]}/DeVS_{F[1,2]}$ interaction is weaker compared to the $KdpD_{F[3]}/KdpE_{F[1,2]}$, and $Esat-6_{F[3]}/Cfp-10_{F[1,2]}$ interactions (shown below). Therefore, M-PFC is effective in detecting association between a membrane spanning sensor protein, and the corresponding cytoplasmic response regulator.

In order to determine whether M-PFC is influenced by the N- or C-terminal orientation of the small $F_{[1,2]}$ or $F_{[3]}$ fusions, Esat-6 and Cfp-10 were cloned into pUAB100, pUAB300 and pUAB200, pUAB400 to generate $Esat-6_{F[1,2]}$, $_{F[1,2]}Esat-6$ and $Cfp-10_{F[3]}, _{F[3]}Cfp-10$ fusions, respectively. As shown in FIG. 5B, clones co-transformed with plasmids generating $Esat-6_{F[1,2]}/Cfp-10_{F[3]}$, and $_{F[1,2]}Esat-6_{F[3]}Cfp-10$ showed robust growth whereas the controls showed no growth on 7H11/KAN/HYG/TRIM. Therefore, M-PFC is a flexible and robust system that is only marginally affected by the orientation of the DHFR peptides, at least for Esat-6 and Cfp-10.

Figure 6:
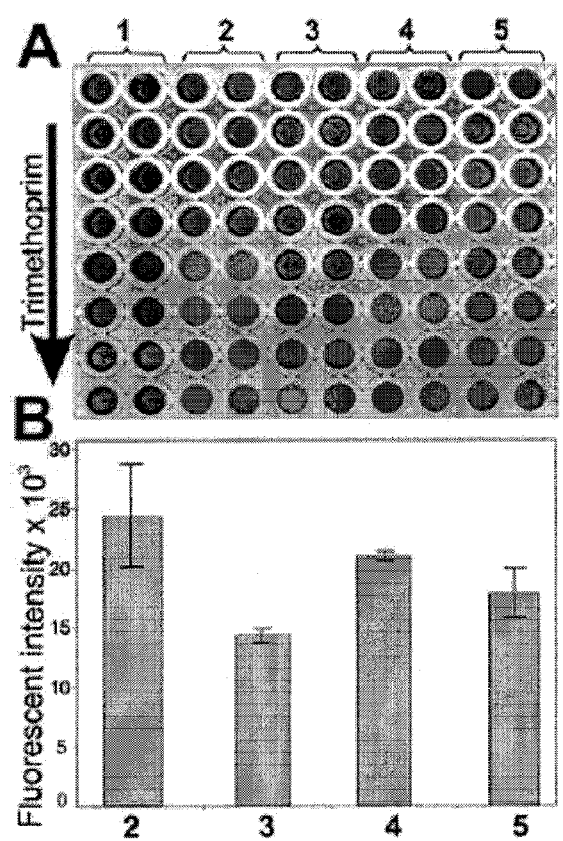
FIG. 6A shows an adapted Alamar Blue fluorescent assay in a 96-well microtiter plate (as discussed in Example 1) for Msm cells co-transformed with plasmids producing the protein partners (1) hsp60$_{[F1,2]}$hsp60$_{[F3]}$ (2) GCN4$_{[F1,2]}$/GCN4$_{[F3]}$, (3) DevS$_{[F1,2]}$/DevR$_{[F3]}$, (4) Esat-6$_{[F1,2]}$/Cfp-10$_{[F3]}$ and (5) KdpD$_{[F1,2]}$/KdpE$_{[F3]}$ (in which a change from non-fluorescent blue (darker shading) to fluorescent pink (lighter shading) indicates reduction of Alamar Blue and is indicative of protein-protein interaction).
FIG. 6B shows the change in color intensity in the microtiter plate shown in FIG. 5A (as measured at 580 nm using an excitation wavelength of 530 nm).

The results showed that reconstitution of mDHFR due to protein-protein association in Msm can be easily monitored by a survival-based assay on 7H11/KAN/HYG/TRIM plates. However, to study the effect of single aa substitutions or modifications (e.g., phosphorylation) on protein-protein association, or performing domain mapping experiments, requires a more sensitive and quantitative assay. As a result, a colorimetric and fluorescent plate-based assay was developed and optimized. The assay is based on the oxidation/reduction indicator Alamar Blue (AB) that has been widely used in quantitative and qualitative assays to assess sensitivity of mycobacteria to antimycobacterial compounds (McNerney et al. (2000) *Int J Tuberc Lung Dis* 4, 69-75). The AB assay quantitatively measures the proliferation of human and animal cell lines, bacteria and fungi (Back et al. (1999) *J Neurosci Methods* 91, 47-54; Collins et al. (1997) *Antimicrob Agents Chemother* 41, 1004-9) and can easily be performed in 96-well format. Msm harboring the interacting clones $GCN4_{[F1,2]}/GCN4_{[F3]}$, $KdpD_{[F1,2]}/KdpE_{[F3]}$, $Esat-6_{[F1,2]}/Cfp-10_{[F3]}$ and $DevR_{F[3]}/DevS_{F[1,2]}$ were cultured in 7H9/HYG/KAN and freshly inoculated into 96-well microtiter plates containing 7H9/KAN/HYG/TRIM. A change from non-fluorescent blue (darker shading) to fluorescent pink color (lighter shading) indicates reduction of AB and the intensity of pink color directly correlates with the extent of bacterial growth, which in turn depends upon the degree of reconstitution of F[1,2] and F[3] driven by the interacting proteins (FIG. 6). Msm clones containing interacting partners grew in 7H9/KAN/HYG/TRIM media as was evident by the development of a pink color (lighter shading) due to the reduction of AB (FIG. 6). More importantly, there was no color change observed in the vector control confirming the specificity of the assay. Furthermore, to accurately measure the strength of interaction, fluorescence was quantified at an excitation wavelength of 530 nm and an emission wavelength of 580 nm. As shown in FIG. 6, it was found that GCN4$_{[F1,2]}$/GCN4$_{[F3]}$, interact the strongest, followed by Esat-6$_{[F1,2]}$/Cfp-10$_{[F3]}$ and KdpD$_{[F1,2]}$/KdpE$_{[F3]}$ and lastly DevR$_{F[3]}$/DevS$_{F[1,2]}$. The M-PCF system can be utilized to detect a broad range of protein-protein associations in mycobacteria.

Figure 7:
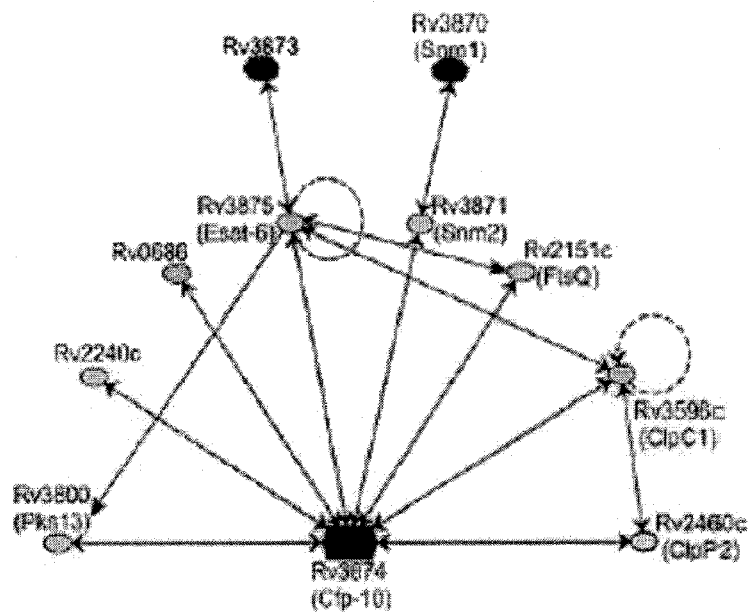
FIG. 7 shows a graph (generated using Yed graph editor software) indicating protein associations identified and/or confirmed by the M-PFC technique. The dotted arrows indicate self-association. The outer nodes refer to an Y2H study whereas the inner nodes refer to novel interactions found herein.

Protein interaction technologies directly link genes involved in particular virulence pathways or signaling cascades irrespective of whether they are essential or not. In order to verify and test the applicability of M-PFC to study virulence mechanisms previously not amenable to standard mycobacterial methods, the Mtb Cfp-110/Esat-6 secretion pathway was analyzed. Both Esat-6 and Cfp-10 are secreted through an undefined Mtb secretion mechanism known as the signal peptide independent secretion (SPS) system. Cfp-10 is the major T-cell antigen encoded by esxB (Rv3874) present in the RD1 region, and is required for full virulence of Mtb. The hypothesis that M-PFC can identify additional, essential gene products that participate in the secretion of Esat-6 and Cfp-10 and can contribute towards understanding the mechanism of SPS in Mtb was tested. Subsequently, full length cfp-10 was cloned in frame with F[3] in the stable, integrative M-PFC bait vector to generate pUAB400-Cfp10. An Mtb H37Rv genomic DNA library, consisting of 5×10⁵ independent clones was made in pUAB300, transformed into Msm cells containing pUAB400-Cfp10, and plated on 7H11/KAN/HYG/TRIM. Colonies that showed growth on 7H11/KAN/HYG/TRIM plates were lysed, plasmid DNA isolated, amplified in *E. coli* and again transformed into Msm containing pUAB400-Cfp10. Clones were again streaked on 7H11/KAN/HYG/TRIM plates and assessed for growth. Library plasmids from clones that show growth on TRIM plates were sequenced. As anticipated, TRIM resistant clones containing Mtb dfrA (Rv2763c) was observed in the library. Conveniently, these TRIM resistant clones act as internal controls for library complexity and transformation efficiency and colony-PCR was used to eliminate these clones. Additionally, Esat-6, the known partner of Cfp-10, was identified six times in the library screens. These results demonstrate that M-PFC can effectively be exploited to identify interacting clones from an Mtb library. Also, the specificity of these interactions was verified by (i) determining the ability of individual Cfp-10$_{[F1,2]}$ interacting proteins to associate with unrelated proteins (e.g., KdpE), and (ii) co-transformation of Cfp-10$_{[F1,2]}$ interacting clones with the corresponding empty vector. In all cases, no growth was observed on 7H11/TRIM plates, thereby confirming the specificity of the interactions. Proteins that associate with Cfp-10 are listed in Table 1. In the screen, multiple overlapping clones of the same gene were identified, thereby providing support that the association is indeed true. Subsequent cloning of snm2 (Rv3871) and M-PFC analysis demonstrated that 5 nm2 associate strongly with Cfp-10 (FIG. 7). Since Esat-6 and Cfp-10 form a tight complex, it was hypothesized that the Cfp-10 interacting proteins can also associate with Esat-6. Indeed, of the six Cfp-10 interacting clones, Pks13, ClpC1, FtsQ (and Cfp-10) specifically associate with Esat-6 (Table 2). Intriguingly, the data show that Esat-6 oligomerizes (FIG. 7). To further investigate the role of ClpC1, it was demonstrated that ClpC1 associates with the proteolytic component ClpP2, but not ClpP1 (FIG. 7). Taken together, 56% of the putative interacting clones contained Mtb dhfr, 24% of the clones represent anti-sense and out-of-frame clones, and 20% of the clones contained in-frame clones.

TABLE 1

Cfp-10 interacting Mtb proteins identified in a M-PFC screen.

| Rv no. | Gene | Annotation and putative function |
|---|---|---|
| Rv3875[a] | esat-6 | Secreted antigen, known Cfp-10 interacting clone |
| Rv0686[b] | | Belongs to COG0541 that contains members of the SRP-GTPase family. The family includes SRP and its receptor, which targets membrane proteins to bacterial or eukaryotic membranes for insertion; contains required IMP/GMP reductase domain and hydrophobic N-terminus. |
| Rv2151c[c] | ftsQ | Cytoplasmic membrane protein; plays a role in cell division, delivered to membrane via SRP pathway and interacts with SecYEG translocase during insertion into the membrane. |
| Rv3596c[d] | clpC1 | AAA-ATPase chaperone with dual function: (i) ortholog of a component of protein translocation complex present in the outer and inner chloroplast and it can facilitate translocation of precursor proteins across membranes via ClpC-dependant ATP hydrolysis, or (ii) is involved in protein quality control by retro-translocating misfolded proteins into the degradation chamber of the proteolytic subunit, ClpP. |
| Rv3800c[e] | pks13 | Polyketide synthase that catalyzes the last step of mycolic acid biosynthesis. Contains acyltransferase domain. |
| Rv2240c[f] | | Membrane protein of unknown function. |

[a]Two classes of overlapping clones were identified; fusion junction at Esat-6 aa 9 and aa 13.
[b]Two classes of overlapping clones were identified; fusion junction at Rv0686 aa 201 and aa 334.
[c]One class of interacting clone was identified; fusion junction at FtsQ aa 220.
[d]Four classes of overlapping clones were identified; fusion junction at 29, 38, 59 and 117 bp upstream of ATG generated an in-frame fusion with ClpC1.
[e]One class of interacting clone was identified; fusion junction at Pks13 aa 1340.
[f]One class of interacting clone was identified; fusion junction at Rv2240c aa 127.

The M-PFC system, as disclosed herein, allows for the study of Mtb virulence mechanisms and other functional pathways through protein-protein association. In this approach, the independent genetic coupling of mDHFR complementary fragments ([F1,2] and [F3]) with two mycobacterial interacting proteins leads to the reconstitution of the mDHFR activity in vivo, at a concentration where endogenous mycobacterial DHFR activity is inhibited. The readout of this complementation event is the in vivo reconstitution of mDHFR fragments F[1,2] and F[3] that allow for the selection of mycobacterial clones resistant to TRIM. Importantly, only when F[1,2] and F[3] are fused with two interacting proteins, will heterodimerization result in reconstitution of mDHFR. The M-PFC system was thoroughly tested using well documented and known protein-protein interactions such as eukaryotic GCN4, as well as the protein interactions of Mtb KdpD/KdpE, and DevR/DevS, and the secretory antigens Esat-6 and Cfp-10. Using a number of controls including unrelated proteins and empty vectors, it was confirmed that these proteins specifically associate in mycobacteria. The system proved to be sufficiently sensitive and robust to study the presumably transient association between membrane located sensor kinases (KdpD and DevS) and their corresponding response regulators (KdpE and DevR), respectively. Moreover, it seems that the orientation of fusions has little or no effect on the refolding of F[1,2] and F[3] for at least Esat-6/Cfp-10. However, it is expected that some proteins may require a free N or C-terminus for interactions which will have to be tested individually. An important advantage of studying protein association in mycobacteria rather than surrogate hosts such as yeast and E. coli is that appropriate modifications (e.g., phosphorylation), co-factors, and the exclusive intracellular environments unique to the natural host, can modulate the outcome of interactions.

Virulence pathways are mediated by complex networks of molecular interactions, which upon disruption, alter protein-protein associations. Thus, protein-protein interactions typically suggest a direct link or role, whereas gene disruption experiments are an indirect measure. As a result, one of the central aims of this study was to test the capacity of M-PFC to study undefined Mtb virulence mechanisms. Several studies (Fortune et al. (2005) Proc Natl Acad Sci USA 102, 10676-81; Brodin et al. (2006) Infect Immun 74, 88-98; Pym et al. (2002) Mol Microbiol 46, 709-17) have shown that proteins in and outside the Mtb RD1 region are involved in secretion of the immunogenic antigens, Esat-6 and Cfp-10. An important feature of the SPS system is that these small proteins contain no signal peptide. Subsequently, the Mtb SPS pathway is characterized by performing a genome-wide screen for Cfp-10 interacting clones. Esat-6 was repeatedly identified as one of its interacting partners, which is consistent with previous studies (Renshaw et al. (2002) J Biol Chem 277, 21598-603; Stanley et al. (2003) Proc Natl Acad Sci USA 100, 13001-6; Okkels et al. (2004) Proteomics 4, 2954-60) and validates M-PFC as an effective tool to screen the Mtb genome for interacting proteins. More importantly, several components of the Mtb secretory pathway were identified. For example, Rv0686, a member of the SRP-GTPase family was shown to specifically interact with Cfp-10. Members of this family include SRP and its receptor, SR and are involved in cotranslational targeting of proteins in the bacterial plasma membrane and eukaryotic ER membrane for secretion or membrane insertion (Keenan et al. (2001) Annu Rev Biochem 70, 755-75). In the gram positive bacterium, Bacillus subtilis, both SRP and SR are involved in targeting the majority of the secreted proteins to the Sec translocase (Yamane et al. (2004) Biosci Biotechnol Biochem 68, 2007-23). The data show that the SRP-GTPase ortholog (Rv0686) can facilitate targeting of Cfp-10 to the membrane via the SRP pathway. In support of the above results, a second substrate of the SRP pathway, the cell division protein FtsQ (Rv2921c), was identified, which has been widely used as a model protein to dissect SRP dependent translocation of integral membrane proteins (Urbanus et al. (2001) EMBO Rep 2, 524-9). Importantly, it is known that during the membrane insertion process, FtsQ interact with components of SecYEG translocon. Thus, it is possible that FtsQ participate in the delivery of Cfp-10 to the SecYEG translocon. Furthermore, a positive interaction between Cfp-10 and the AAA-ATPase chaperone ClpC1 that belongs to the Clp/Hsp100 family of proteins was also detected. Members of the Clp family are involved in diverse functions including secretion, gene regulation, protein refolding, and degradation (Bolhuis et al. (1999) J Biol Chem 274, 24585-92; Porankiewicz et al. (1999) Mol Microbiol 32, 449-58). Interestingly, it has been shown that ClpC homologues play a crucial role in the protein import pathway in plants by associating with the translocation machinery in the chloroplast membrane (Nielsen et al. (1997) Embo J 16, 935-46). Mtb ClpC1 can facilitate Cfp-10 secretion by associating with the translocation complex in the membrane. In addition, ClpC can also play an important role in quality control of translated proteins by targeting misfolded proteins into the chamber of proteolytic subunit, ClpP for degradation (Pan, Q. & Losick, R. (2003) J Bacteriol 185, 5275-8). The fact that ClpC1 selectively associate with the ClpP2 (Rv2460c) protease subunit (FIG. 6), but not with other proteolytic subunits (e.g. ClpP1) or unrelated control proteins, shows that the association is specific.

The association of Esat-6 and Cfp-10 with Pks13 shows that the interaction is physiologically relevant especially since it was previously demonstrated that acetylation affects the interaction of Cfp-10 with Esat-6. It was hypothesized that the acyltransferase (AT) domain in the Pks13 can modify Cfp-10 by acylation. Interestingly, N-terminal acylation of eukaryotic proteins occurs frequently and is required for proper translocation of proteins that lack a recognizable secretory signal sequence. Cfp-10 contains an Ala after the Met at the N-terminus whereas Esat-6, the known partner of Cfp-10, is acetylated at the N-terminal Thr residue. In eukaryotes, these amino acids accounts for ~95% of the N-terminus acetylated residues.

In sum, M-PFC enables the shedding of light on the mechanism of protein secretion in Mtb and identified several novel components of the Cfp-10 secretory pathway. The results directly link the Mtb SPS pathway with the evolutionary conserved SRP and SecA/SecYEG pathways, and provide strong evidence for an overlap between these pathways, showing that they can share secretory components. Also, the fact that M-PFC can implicate essential gene products such as FtsQ, ClpC1, and the SecYEG complex in the Mtb SPS pathway, demonstrates the potential of M-PFC to dissect virulence mechanisms that is not amenable by gene disruption strategies.

Methods

Strains and Media. Cultivation and transformation of Mtb H37Rv and Msm mc$^2$155 were performed as described previously (Wards, B. J. & Collins, D. M. (1996) FEMS Microbiol Lett 145, 101-5). When necessary, Middlebrook media (MB) was supplemented with kanamycin (25 μg/ml), hygromycin (50 μg/ml), or trimethoprim (40-50 μg/ml). E. coli DH10B was grown in LB supplemented with kanamycin (25 μg/ml) or hygromycin (150 μg/ml).

Plasmid constructs for M-PFC. The plasmids pKSFR(1,2) and pKSFR(3) contain mDHFRF(1,2) (F[1,2]) and mDHFRF(3) (F[3]) respectively, fused in-frame with a 10-amino acid flexible Gly linker (Gly$_{10}$) and GCN4 leucine zipper coding sequence, were used as templates for generating M-PFC plasmids. Complementary oligonucleotides containing the restriction enzyme sites BamHI and AccI were used to PCR amplify F[1,2] along with a flexible Gly linker and leucine zipper (GCN4) sequences (GCN4-[Gly]$_{10}$-F[1,2]). The PCR fragment was digested and ligated to BamHI/ClaI digested pMV261 generating the episomal vector pUAB100. Similarly, a PCR amplicon containing F[3] along with the flexible glycine linker and GCN4 sequences (GCN4-[Gly]$_{10}$-F[3]) was digested and ligated with MfeI/HpaI digested pMV361 to generate the integrating vector pUAB200. These constructs contain the GCN4 homo-dimerization domains fused to the N-terminus of mDHFR fragments. When necessary, the GCN4 domains from pUAB100 and pUAB200 were replaced with bait or prey DNA sequences. For library screens, the M-PFC vectors were modified by cloning the F[3]-[Gly]$_{10}$ sequence into the E. coli-mycobacterial shuttle vector pMV761 to generate the integrating vector pUAB400. Similarly, the complementary fragment of mDHFR, i.e., F[1,2], along with a flexible glycine linker (F[1,2]-[Gly]$_{10}$) was PCR amplified, and cloned in pMV762 to create the episomal plasmid pUAB300.

pUAB100 and pUAB300 are episomal mycobacterial-E. coli shuttle plasmids whereas pUAB200 and pUAB400 are integrating mycobacterial-E. coli shuttle plasmids. The preferred plasmid choice for making DNA libraries is pUAB300. F[1,2] and F[3] are the complementary fragments of mDHFR, GCN4 is the S. cerevisiae leucine zipper sequence, (GLY)$_{10}$ is the flexible 10 amino acid Gly linker, aph confers resistance to kanamycin, hyg confers resistance to hygromycin, hsp60$_p$ is the hsp60 promoter, oriM is the origin of replication for propagation in mycobacteria, oriE is the origin of replication for propagation in E. coli, and int and attP are from mycobacteriophage L5.

M-PFC Library Screen. The Mtb genomic DNA library containing 5×10$^5$ independent clones was prepared and cloned into the unique ClaI site of pUAB300. The bait plasmid was constructed by PCR amplifying cfp-10 and subsequent ligation to MunI/ClaI linearized pUAB400 to create pUAB400-cfp10. The bait plasmid was transformed into Msm, and electroporated with the Mtb library DNA. Interacting clones were selected by plating transformants on 7H11 media containing KAN, HYG and TRIM (50 µg/ml).

Alamar blue assay. Msm clones containing interacting plasmids were cultured in MB 7H9 medium containing HYG and KAN to an OD$_{600nm}$ of 0.8. Cells were diluted in fresh 7H9 medium, and ~10$^6$ cells were added to clear bottom, 96 well microtiter plates. Outer perimeter wells were filled with sterile water to prevent dehydration. TRIM was dissolved in dimethylsulfoxide and two-fold serial dilutions of the drug were made in 0.1 ml of 7H9 in microtiter plates. Wells containing drug only and no Msm cells were the autofluorescence controls. Additional controls consisted of wells containing cells and medium only. Plates were incubated for 12 h after which 30 µl of Alamar Blue (Biosource International; Camarillo, Calif.) solution (1:1 dilution in MB 7H9-tween medium) was added to wells containing cells only, incubated and observed for the appearance of a pink color. Alamar Blue was added to each well after the emergence of a pink color in the cells only wells. Plates were further incubated at 37° C., and the result recorded after 6 h. Fluorescence intensity was measured in a Cytofluor CYTOFLUOR® II microplate fluorometer (PerSeptive Biosystems; Framingham, Mass.) in bottom reading mode with excitation at 530 nm and emission at 590 nm. Msm transformants containing empty vectors hsp60$_{[F1,2]}$/hsp60$_{[F3]}$ show a low level of background fluorescence.

Yed graph editor. The network of proteins that associate with the Cfp-10 was generated using Yed graph editor software (www.yWorks.com; Tübingen, Germany).

Figure 8:
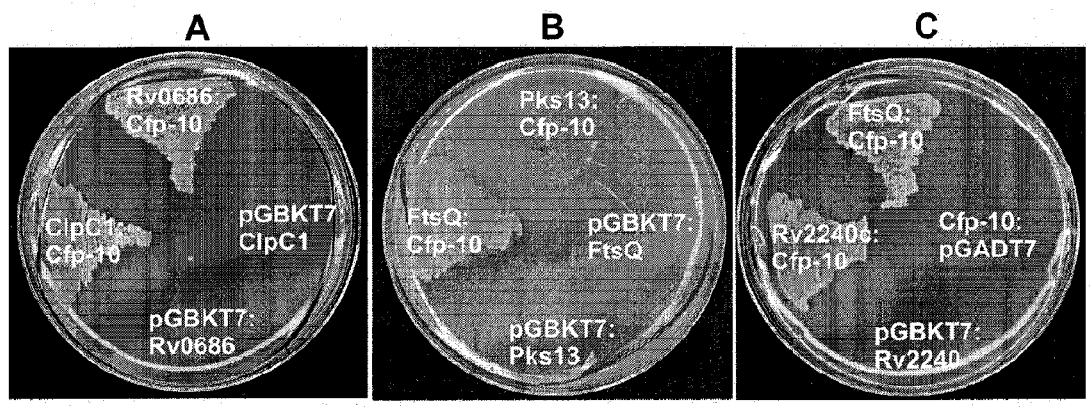
FIG. 8A shows Y2H data demonstrating the interaction of Mtb Cfp-10 with proteins identified in an M-PFC screen in *S. cerevisiae* clones grown on SC media lacking Ade, Leu, and Trp, but supplemented with x-•-Gal. The combinations were: 1) *S. cerevisiae* [Cfp-10/ClpC1] 2) *S. cerevisiae* [Cfp-10/Rv0686] 3) *S. cerevisiae* [pGBKT7/ClpC1] 4) *S. cerevisiae* [pGBKT7/Rv0686].
FIG. 8B shows Y2H data demonstrating the interaction of Mtb Cfp-10 with proteins identified in an M-PFC screen in *S. cerevisiae* clones grown on SC media lacking Ade, Leu, and Trp, but supplemented with x-•-Gal. The combinations were: 1) *S. cerevisiae* [Cfp-10/FtsQ] 2) *S. cerevisiae* [Cfp-10/Rv3800c] 3) *S. cerevisiae* [pGBKT7/Rv3800c], 4) *S. cerevisiae* [Cfp-10/pGADT7].
FIG. 8C shows Y2H data demonstrating the interaction of Mtb Cfp-10 with proteins identified in an M-PFC screen in *S. cerevisiae* clones grown on SC media lacking Ade, Leu, and Trp, but supplemented with x-•-Gal. The combinations were: 1) *S. cerevisiae* [Cfp-10/Rv2240c], 2) *S. cerevisiae* [Cfp-10/FtsQ], 3) *S. cerevisiae* [pGBKT7/FtsQ] 4) *S. cerevisiae* [pGBKT7/Rv2240c].

Y2H Analysis. Despite the fact that multiple overlapping clones were identified in the Cfp-10 screen, a finding which strongly shows that the interactions are biologically significant, the Y2H system was used to independently verify the Cfp-10/ClpC1, Cfp-10/Pks13, Cfp-10/FtsQ Cfp-10/Rv2240c and Cfp-10/Rv0686 interactions (FIG. 8). The Y2H data confirmed that Cfp-10/ClpC1, Cfp-10/FtsQ, Cfp-10/Rv2240c, and Cfp-110/Rv0686 do indeed associate. Note that none of the clones identified in the M-PFC screen, nor Cfp-10, were capable of self-activation in the Y2H system.

Saccharomyces cerevisiae strains (PJ69-4A and PJ69-4α) were cultured as described previously. The bait and prey plasmid pGBKT7 and pGADT7 (Clontech, Calif.), were used to generate two-hybrid fusion constructs. Complementary oligonucleotides containing the restriction enzyme sites NcoI and BamHI were used to PCR amplify full length cfp-10 (bait) and preys. Bait and prey fusion constructs were verified by sequencing and co-transformed into S. cerevisiae PJ69-4α. In S. cerevisiae PJ69-4, GAL4 regulates ADE2, HIS3 as well as MEL1 which encodes for α-galactosidase thereby enabling the validation of the specificity of interaction by screening for blue color formation on synthetic complete (SC) plates lacking Ade and His containing 5-bromo-4-chloro-3-indolyl-α-D-galactopyranoside (X-α-Gal) (20 µg/ml). Yeast transformants were selected on SC-Leu Tip at 30° C. S. cerevisiae cells were plated on X-α-gal plates containing SC-Leu-Trp-Ade plates (FIG. 8).

Example 2

Screening a Small Molecule Compound Library Using M-PFC

The M-PFC screening system described herein was used to search for small-molecule inhibitors of DevR (also known as DosR or Rv3133c) dimerization using the Alamar blue assay described above. The assay reflected the effect of an inhibitor on viability and/or protein-protein interactions based on a significant decrease (3× standard deviation) in fluorescence emitted at 490 nm when compared to a control. Compounds that effected viability were separated from the compound pool for screening.

Figure 9:
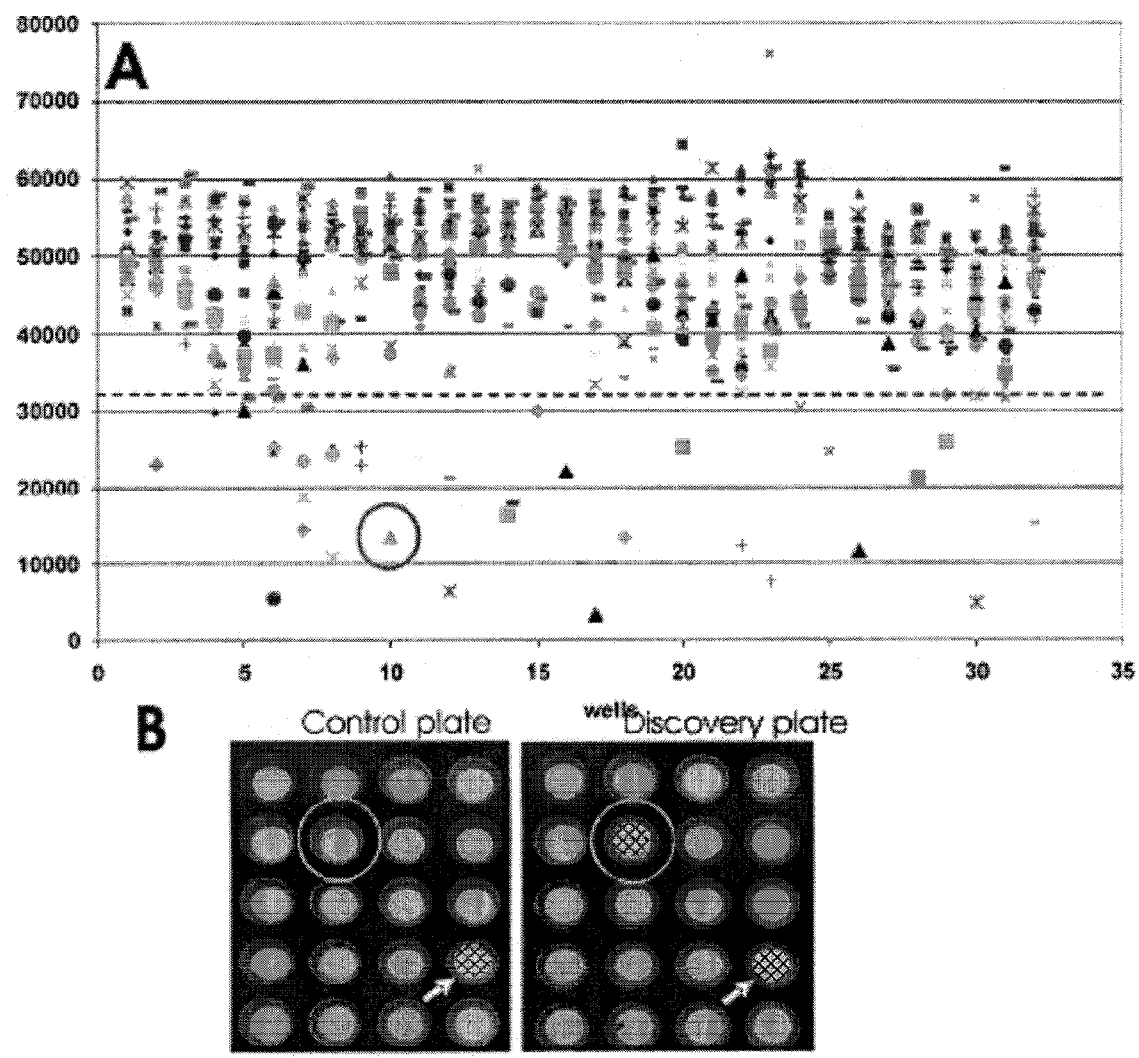
FIG. 9A shows the data from a library screening experiment to identify small molecules that inhibit DevR dimerization and FIG. 9B shows an example control/discovery plate set up with the arrow representing a false positive on the discovery plate and the white circles representing a positive hit on the discovery plate (with positive hits indicated in FIG. 9B as cross-hatching).

A 1000-compound library separated from a DIVERSet™ library from Chembridge (San Diego, Calif.) was initially screened at 12.5 µg/mL against Rv3133c dimerization interaction. This screen yielded 17 candidates that did not effect cell viability. FIGS. 9A and 9B show the data for this screen. In FIG. 9A, data obtained in the screen was normalized with data obtained in a control screen. FIG. 9B shows segments of scanned control and discovery plates. In FIG. 9B, white circles indicate a hit that corresponds to the circled data point in FIG. 9A (as identified by the difference in fluorescence intensities of the respective wells in the plates with positive hits in this figure shown by cross hatch). The white arrows in FIG. 9B indicate a compound that does not target DevR dimerization, but that kills cells in both the control and discovery plates.

Figure 10:
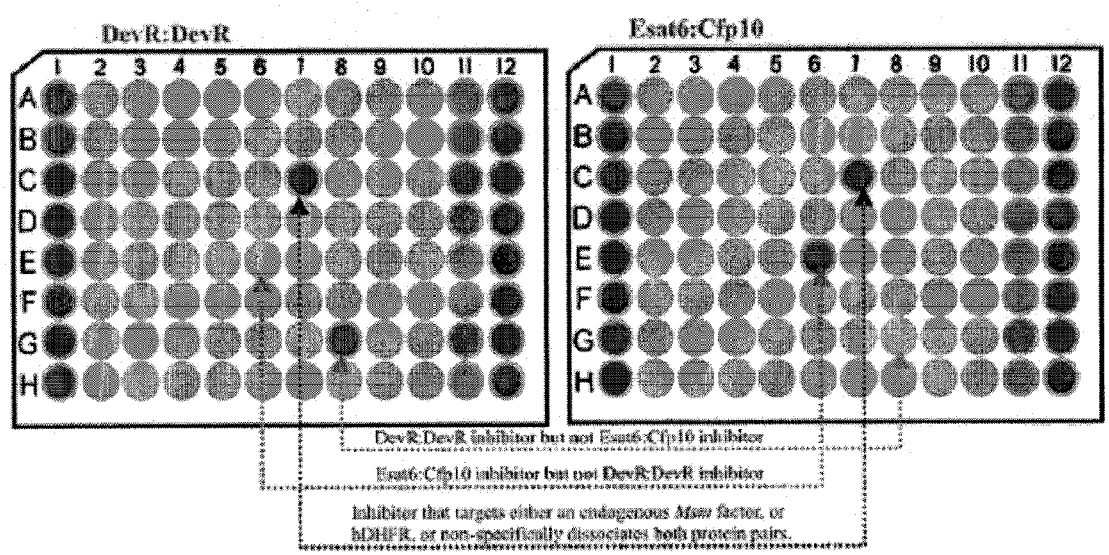
FIG. 10 shows an example two plate set up for a M-PFC Alamar Blue TRIM counter screen assay.

An extensive counter-screen was performed with Esat6-Cfp10 (Rv3875-Rv3874), a know interacting pair, to eliminate candidates that targeted the reporter enzyme (DFHR). FIG. 10 shows an illustration of the set up for a M-PFC Alamar Blue TRIM counter screen assay. In FIG. 10, the dotted lines indicate hypothetical examples of inhibitors of protein-protein association. In FIG. 10, the DevR:DevR screen acts as a counter-screen for the Esat6-Cfp10 screen (and vice versa). The solid blue columns (lanes 1 and 12; darker shading) in FIG. 10 are the AB alone controls for contamination and the edge effect. Lanes 11 in FIG. 10 are the interacting clones with TRIM, but no compound. The pink color (lighter shading) in FIG. 10 indicates viable cells, whereas blue (darker shading) indicates dead cells.

Figure 11:
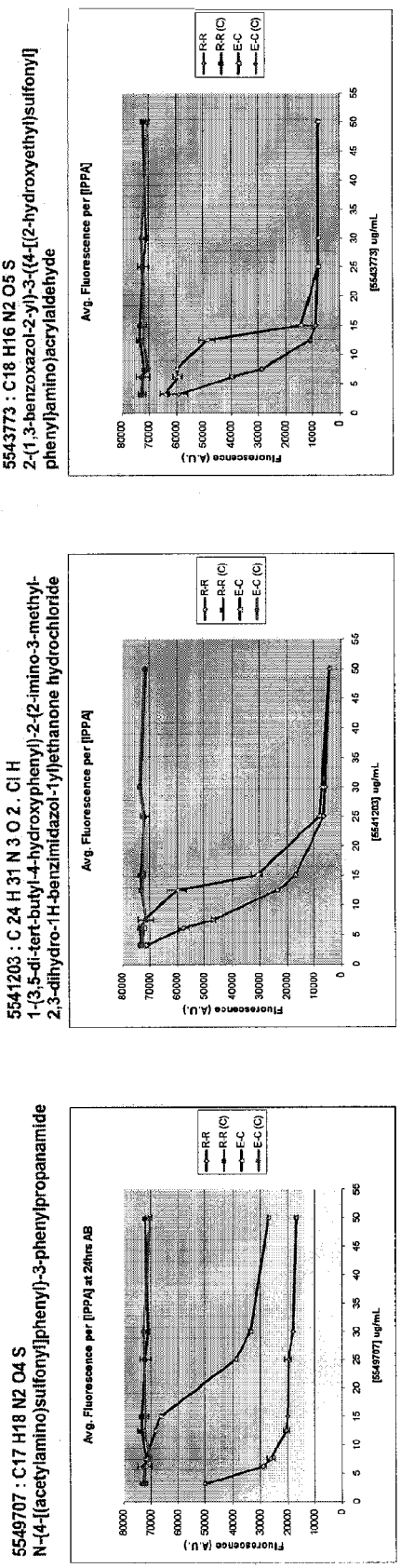
FIG. 11 shows titration curves for molecules identified in a screening experiment to identify small molecules that inhibit DevR dimerization.

Three compounds were identified by this screen: N-(4-[(acetylamino)sulfonyl]phenyl)-3-phenylpropanamide; 1-(3,5-di-tert-butyl-4-hydroxyphenyl)-2-(2-imino-3-methyl-2,3- dihydro-1H-benzimidazol-1-yl)ethanone hydrochloride; and 1-(1,3-benzoxazol-2-yl)-3-({4-[(2-hydroxyethyl)sulfonyl] phenyl}amino)acrylaldehyde (the structures for these compounds are shown below). Each of these compounds exhibited inhibitory effect against DevR dimerization at low concentrations. FIG. 11 shows titration curves for these compounds. All three compounds have the most dramatic effect on DevR dimerization at 12.5 µg/mL. 1-(3,5-di-tert-butyl-4-hydroxyphenyl)-2-(2-imino-3-methyl-2,3-dihydro-1H-benzimidazol-1-yl)ethanone hydrochloride and 1-(1,3-benzoxazol-2-yl)-3-({4-[(2-hydroxyethyl)sulfonyl]phenyl}amino) acrylaldehyde were found to effect cell viability at high concentrations.

Figure 12:
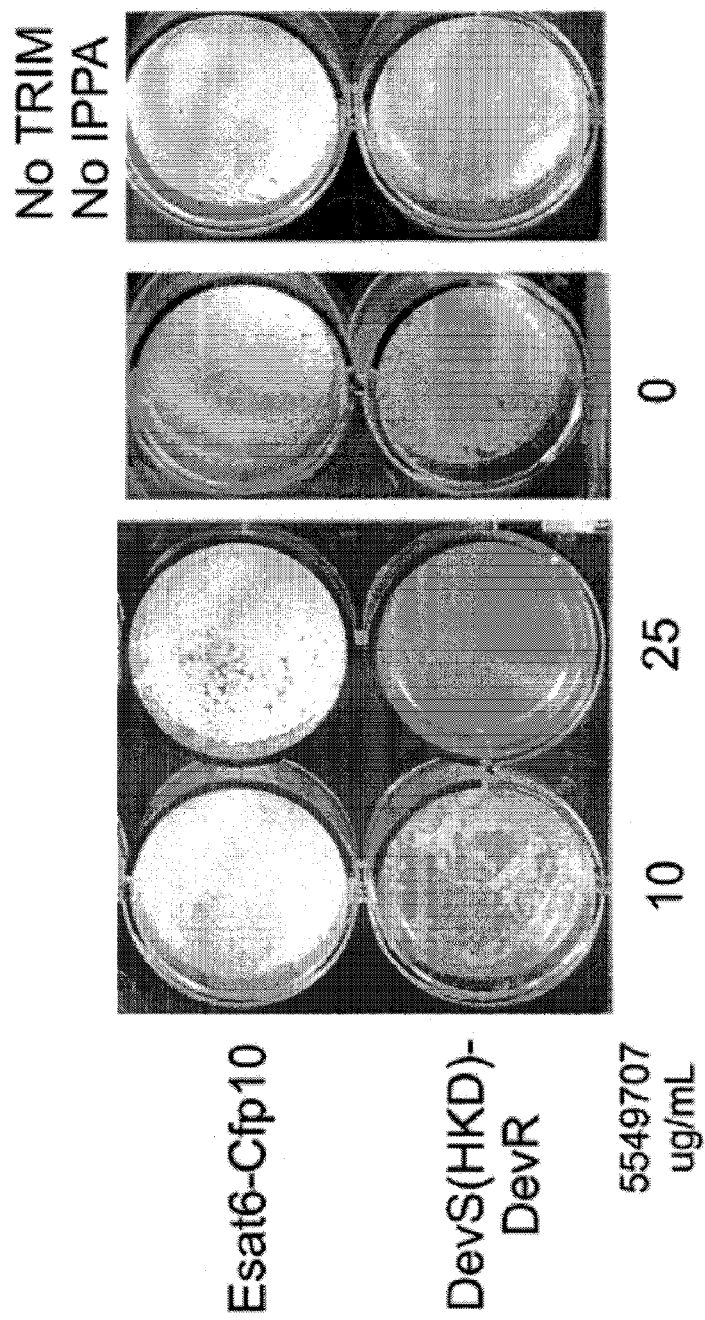
FIG. 12 shows experimental plates indicating that N-(4-[(acetylamino)sulfonyl]phenyl)-3-phenylpropanamide is capable of disrupting the DevS(HKD)-DevR interaction.

Additionally, whether inhibition of DevR dimerization effected upstream interactions with DevR and DevS (Rv3132c), a corresponding sensor histidine kinase involved in the *Mycobacterium* dormancy pathway was investigated. N-(4-[(acetylamino)sulfonyl]phenyl)-3-phenylpropanamide was found to be capable of disrupting the DevS(HKD)-DevR interaction, as shown in FIG. 12. In FIG. 12, N-(4-[(acetylamino)sulfonyl]phenyl)-3-phenylpropanamide is shown to disrupt the DevS(HKD)-DevR interaction at 10 and 25 µg/mL concentrations, whereas the Esat6-Cfp10 interaction remains unaffected. FIG. 12 also shows that both DevS(HKD)-DevR and Esat6-Cfp10 strains grow in the absence of TRIM (plates on right).

Example 3

Rapamycin Induced Protein Interactions in Mycobacterial Cells

Figure 13:
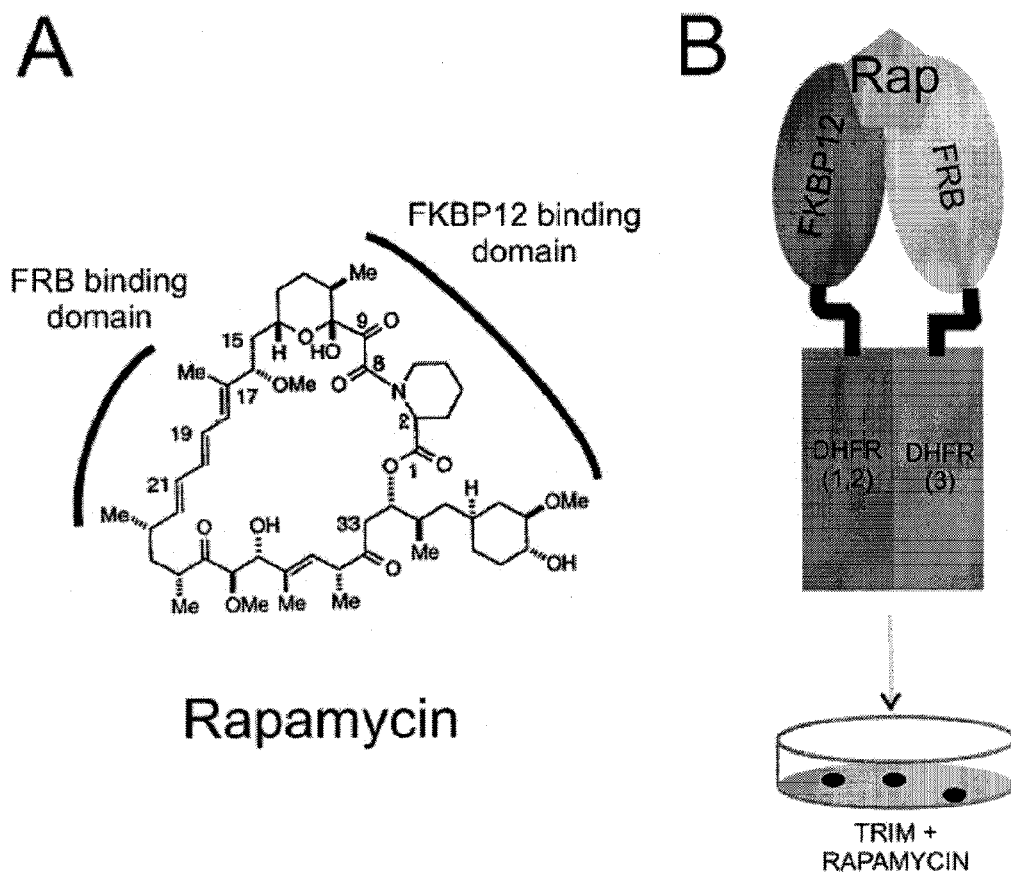
FIG. 13A shows the chemical structure of rapamycin and FIG. 13B shows a rapamycin mediated FRP:rapamycin:FKBP12 complex formed within an M-PFC system.

An M-PFC experiment was run using FRB and FKBP12 fragments as the polypeptide components of the M-PFC fusion proteins. FRB and FKBP are known to interact with rapamycin to form a ternary complex. See Laura A. Banaszynski, Corey W. Liu, and Thomas J. Wandless, "Characterization of the FKBP•Rapamycin•FRB Ternary Complex," *J. Am. Chem. Soc.*, 127 (13), 4715-4721, 2005. The chemical structure of rapamycin indicating the binding regions of rapamycin to FRB and FKBP12 is shown in FIG. 13A. In this system, as illustrated in FIG. 13B, the FKBP12 and FRB fusion proteins form a complex when rapamycin is present bringing the DHFR fragments together, thereby conferring trimethoprim resistance.

Figure 14:
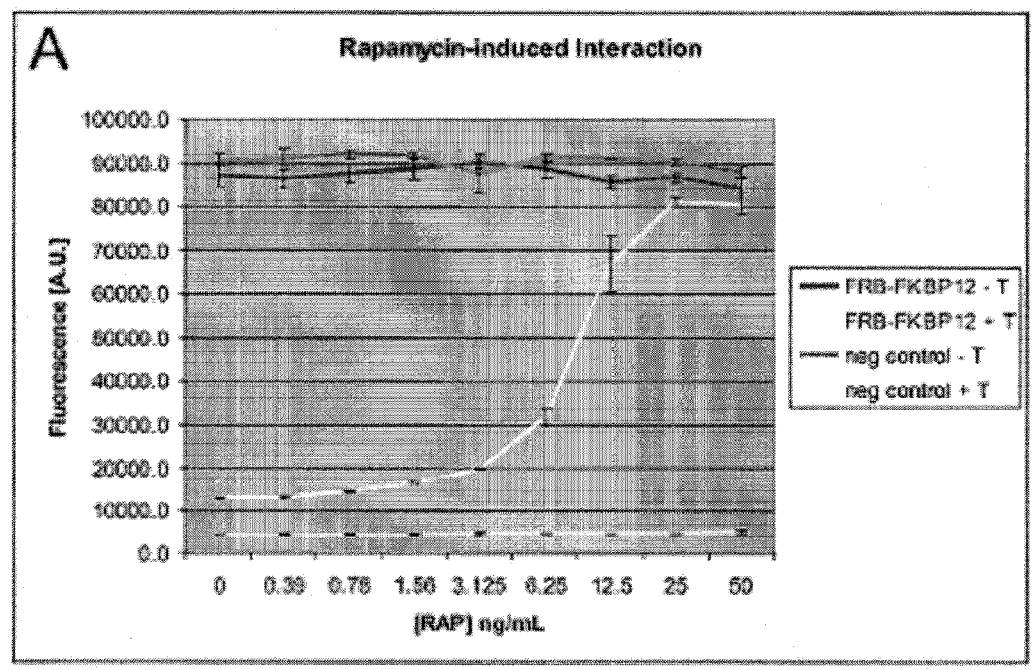
FIG. 14A shows a titration plot of rapamycin-induced interaction between FRP and FKBP12. The experimental data are shown in FIG. 14B.
Figure 14:
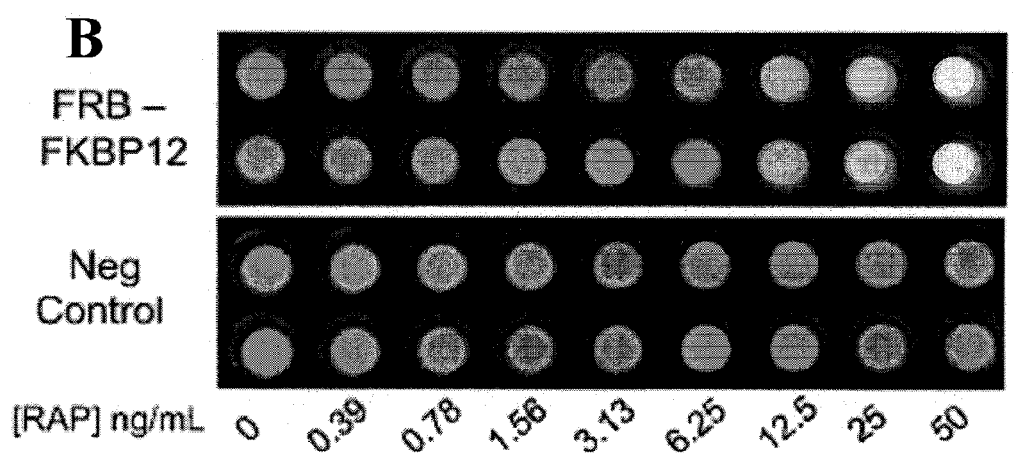

In this experiment, the FRB and FKBP12 fragments associated upon addition of as little as 6.25 ng/mL of rapamycin, which could be measured in a M-PFC Alamar Blue TRIM assay with 20 µg/mL trimethoprim. The M-PFC Alamar Blue TRIM assay experimental data are shown in FIG. 14. FIG. 14B shows the experimental and control plates at varying rapamycin concentrations (TRIM at 20 µg/mL) (lighter shading indicating cell survival). FIG. 14A shows a plot of the rapamycin titration curve data from the plates shown in FIG. 14B. As indicated in the titration curve in FIG. 14A, rapamycin induces interaction at as little as 6.25 ng/mL. Viability of the Mycobacterial cells was not effected at rapamycin concentrations as high as 200 µg/mL. Thus, this experiment demonstrates that rapamycin affinity for FRB and FKBP12 is retained in Mycobacterial cells and that trimethoprim resistance can be conferred in a M-PFC system involving a FRB: rapamycin:FKBP12 ternary complex.

Given that rapamycin forms a ternary complex with FRB and FKBP12, the system shown in FIG. 8 and described above provides a useful drug candidate screening assay. The assay is similar to this experiment in which either FRB or FRBP12 will be replaced with another polypeptide ("Library" or "X" in FIGS. 2A and 2B) and a drug candidate is linked to rapamycin. In the assay, rapamycin forms a complex with the FRB (or FKBP12) polypeptide and if the "Library" or "X" polypeptide has affinity for the drug candidate, a complex forms that reconstitutes the DHFR fragments, thereby conferring trimethoprim resistance.

Any patents or publications mentioned in the specification are indicative of the level of those skilled in the art to which the invention pertains. These patents and publications are herein incorporated by reference to the same extent as if each individual publication was specifically and individually indicated to be incorporated by reference.

The present invention is not limited in scope by the embodiments disclosed in the examples which are intended as illustrations of a few aspects of the invention and any embodiments which are functionally equivalent are within the scope of this invention. Various modifications of the invention in addition to those shown and described herein will become apparent to those skilled in the art and are intended to fall within the scope of the appended claims. Further, while only certain representative combinations of the compositions disclosed herein are specifically discussed in the embodiments above, other combinations of the compositions will become apparent to those skilled in the art and also are intended to fall within the scope of the appended claims.

What is claimed is:

1. A method of treating a *Mycobacterium tuberculosis* or *Mycobacterium leprae* infection in a subject comprising:
    a) detecting in a sample from the subject one or more polypeptides selected from the group consisting of Rv0686 and Rv2240c; and
    b) administering an agent to treat the *Mycobacterium tuberculosis* or *Mycobacterium leprae* infection in the subject.

2. A method of treating a *Mycobacterium tuberculosis* infection in a subject detecting tuberculosis in a subject, comprising the steps of
    (a) contacting an antibody-containing biological sample from the subject with one or more polypeptides selected from the group consisting of Rv0686 and Rv2240c;
    (b) detecting binding of the antibody and the one or more polypeptides, binding indicating tuberculosis in the subject; and
    (c) administering an agent to treat the *Mycobacterium tuberculosis* infection in the subject.

3. A method of treating a *Mycobacterium tuberculosis* infection in a subject comprising:
    (a) detecting in a biological sample from the subject one or a combination of polypeptides selected from the group consisting of Rv0686 and Rv2240c, detection of the polypeptides indicating an infection instead of a memory response generated by vaccination; and
    (b) administering an agent to treat the *Mycobacterium tuberculosis* infection in the subject.

* * * * *

UNITED STATES PATENT AND TRADEMARK OFFICE
CERTIFICATE OF CORRECTION

PATENT NO.        : 8,603,751 B2                                         Page 1 of 1
APPLICATION NO.   : 12/281082
DATED             : December 10, 2013
INVENTOR(S)       : Steyn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 505 days.

Signed and Sealed this
Twenty-first Day of April, 2015

Michelle K. Lee
*Director of the United States Patent and Trademark Office*